(12) United States Patent
Kuninobu et al.

(10) Patent No.: US 10,280,142 B2
(45) Date of Patent: *May 7, 2019

(54) BIPYRIDYL COMPOUND

(71) Applicant: JAPAN SCIENCE AND TECHNOLOGY AGENCY, Kawaguchi-shi (JP)

(72) Inventors: Yoichiro Kuninobu, Bunkyo-ku (JP); Motomu Kanai, Bunkyo-ku (JP); Haruka Ida, Suginami-ku (JP); Mitsumi Nishi, Taito-ku (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/819,180

(22) Filed: Nov. 21, 2017

(65) Prior Publication Data

US 2018/0072672 A1 Mar. 15, 2018

Related U.S. Application Data

(63) Continuation of application No. 15/114,347, filed as application No. PCT/JP2015/052450 on Jan. 29, 2015, now Pat. No. 9,908,852.

(30) Foreign Application Priority Data

Jan. 30, 2014 (JP) ................................ 2014-015211

(51) Int. Cl.
C07D 213/53 (2006.01)
B01J 31/22 (2006.01)
C07F 15/00 (2006.01)
B01J 31/18 (2006.01)

(52) U.S. Cl.
CPC ........ *C07D 213/53* (2013.01); *B01J 31/1815* (2013.01); *B01J 31/22* (2013.01); *C07F 15/0033* (2013.01); *B01J 2231/40* (2013.01); *B01J 2231/4277* (2013.01); *B01J 2531/827* (2013.01)

(58) Field of Classification Search
CPC .................................................. C07D 213/53
USPC ....................................................... 546/265
See application file for complete search history.

(56) References Cited

U.S. PATENT DOCUMENTS 9,908,852 B2 * 3/2018 Kuninobu ................ B01J 31/22

FOREIGN PATENT DOCUMENTS

JP 2012-224575 A 11/2012

OTHER PUBLICATIONS

International Search Report dated Apr. 14, 2015, in PCT/JP2015/052450 Filed Jan. 29, 2015.
Iverson, et al., "Stoichiometric and Catalytic B—C Bond Formation from Unactivated Hydrocarbons and Boranes," Journal of the American Chemical Society, vol. 121, 1999 (2 Pages).
Cho, et al., "Remarkably Selective Iridium Catalysts for the Elaboration of Aromatic C—H Bonds," Science Magazine, vol. 295, 2002, (5 pages).
Cho, et al., "Steric and Chelate Directing Effects in Aromatic Borylation," Journal of the American Chemical Society, vol. 122, 2000, (2 pages).
Tse, et al., "Regioselective Aromatic Borylation in an Inert Solvent," Organic Letters, vol. 3, No. 18, 2001, (3 pages).
Ishiyama, et al., "Iridium-Catalyzed Direct Borylation of Five-Membered Heteroarenes by Bis(pinacolato)diboron: Regioselective, Stoichiometric, and Room Temperature Reactions," Advanced Synthesis & Catalysis, vol. 345, 2003 (4 pages).
Ishiyama, et al. "Mild Iridium-Catalyzed Borylation of Arenes. High Turnover Numbers, Room Temperature Reactions, and Isolation of a Potential Intermediate," Journal of the American Chemical Society, vol. 124, No. 3, 2002, (2 pages).

(Continued)

*Primary Examiner* — Patricia L Morris
(74) *Attorney, Agent, or Firm* — Oblon, McClelland, Maier & Neustadt, L.L.P.

(57) ABSTRACT

There are provided a compound capable of being a novel ligand allowing regioselective borylation to be performed in the aromatic borylation reaction, and a catalyst using the same compound. There is provided a bipyridyl compound represented by a general formula (1): (wherein A represents a single bond, a vinylene group or an ethynylene group;
X represents an oxygen atom or a sulfur atom;
n pieces of $R^1$ may be the same or different, and $R^1$ represents a hydrogen atom, a halogen atom, an optionally substituted hydrocarbon group, an optionally substituted alkoxy group, an optionally substituted aryloxy group, an optionally substituted amino group, a cyano group, a nitro group, or an alkoxycarbonyl group, or two adjacent $R^1$ may form a saturated or unsaturated ring structure optionally containing a hetero atom together with the carbon atoms bonded to the two $R^1$;
$R^2$ represents a hydrogen atom, an optionally substituted hydrocarbon group, an optionally substituted alkoxy group, or an optionally substituted aryloxy group; and
n represents a number of 1 to 4).

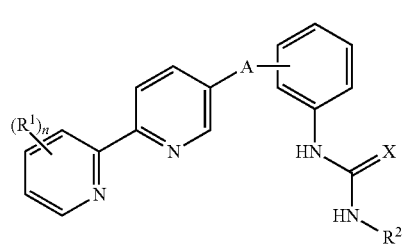

(1)

12 Claims, No Drawings

(56) References Cited

OTHER PUBLICATIONS

Takagi, et al., "Iridium-catalyzed C—H coupling reaction of heteroaromatic compounds with bis(pinacolato)diboron: regioselective synthesis of heteroarylboronates," Tetrahedron Letters, vol. 43, 2002, (3 pages).

Ishiyama, et al., "A Stoichiometric Aromatic C—H Borylation Catalyzed by Iridium(I)/2,2'-Bipyridine Complexes at Room Temperature," Angewandte Chemie International Edition, vol. 41, No. 16, 2002, (3 Pages).

Ishiyama, et al., "Transition metal-catalyzed borylation of alkanes and arenes via C—H activation," Journal of Organometallic Chemistry, vol. 680, 2003, (9 Pages).

Jia, et al., "De Novo Structure-Based Design of Ion-Pair Triple-Stranded Helicates," American Chemical Society, vol. 53, 2014, (6 pages).

Kitchen, et al., "Synthesis, structural characterisation and luminescent anion sensing studies of a Ru(II)polypyridyl complex featuring an aryl urea derivatised 2,2'-bpy auxiliary ligand," Inorganica Chimica Acta, vol. 381, 2012, (7 pages).

Custelcean, et al., "Ion-Pair triple helicates and mesocates self-assembled from ditopic 2,2'-bipyridine-bis(urea) ligands and Ni(II) or Fe(II) sulfate salts," Chemical Communications, vol. 48, (5 pages).

Extended European Search Report dated Jun. 23, 2017 in Patent Application No. 15744067.8.

Yoichiro Kuninobu, et al., "A meta-selective C—H borylation directed by a secondary interaction between ligand and substrate," Nature Chemistry, vol. 7, No. 9, XP55381705, 2015, pp. 712-717.

David A Bardwell, et al., "coordination chemistry of mixed pyridine-phenol ligands. The crystal structure of $[Zn(L^1)_2(BPh_2)]$ $[BPh_4]$ ($HL^1$=6-(2-hydroxyphenyl)-2,2'—bipyridine), the first example of a phenolate bridge between a transition metal and boron," Inorganica Chimica Acta, Elsevier BV, NL, vol. 241, No. 2, XP009161269, 1996, pp. 125-129.

\* cited by examiner

BIPYRIDYL COMPOUND

CROSS-REFERENCE TO RELATED APPLICATIONS

This application is a continuation of U.S. application Ser. No. 15/114,347 filed Jul. 26, 2016, which is pending and which is a National Stage of PCT/JP2015/052450 filed Jan. 29, 2015 and claims the benefit of JP 2014-015211 filed Jan. 30, 2014.

FIELD OF THE INVENTION

The present invention relates to a bipyridyl compound useful as a ligand of a metal catalyst and a catalyst including the same bipyridyl compound as a ligand.

BACKGROUND OF THE INVENTION

The Suzuki-Miyaura reaction performing a cross coupling between an organic halogen compound and an organic boron compound is an important method for carbon-carbon bond formation reaction and is widely applied. The organic boron compound used in this reaction is stable against water or air, and the product of the reaction is a boric acid salt to be thereby low in toxicity and has an advantage of being easily separable from the target product by washing with water.

For the purpose of synthesizing a wide range of compounds by using the Suzuki-Miyaura reaction, it is important to produce compounds each having a boron atom bonded to a specific position in an aromatic compound. In this connection, catalysts such as rhodium catalysts, iridium catalysts and rhenium catalysts are known as the catalysts for the aromatic borylation reactions allowing boron atoms to be bonded to aromatic compounds. In these catalysts, bipyridyl compounds, ethylenediamine compounds, phenanthroline compounds, cyclopentadienyl compounds and the like are used as ligands (Non Patent Literature 1 to Non Patent Literature 9).

CITATION LIST

Non Patent Literature

[Non Patent Literature 1]
 J. Am. Chem. Soc. 1999, 121, 7696
[Non Patent Literature 2]
 Science 2002, 295, 305
[Non Patent Literature 3]
 J. Am. Chem. Soc. 2000, 122, 12868
[Non Patent Literature 4]
 Org. Lett. 2001, 3, 2831
[Non Patent Literature 5]
 Adv. Synth. Catal. 2003, 345, 1103
[Non Patent Literature 6]
 J. Am. Chem. Soc. 2002, 124, 390
[Non Patent Literature 7]
 Tetrahedron Lett. 2002, 43, 5649
[Non Patent Literature 8]
 Angew. Chem. Int. Ed. 2002, 41, 3056
[Non Patent Literature 9]
 J. Organomet. Chem. 2003, 680, 3

SUMMARY OF THE INVENTION

Problem to be Solved by the Invention

However, there has been a problem such that when an aromatic borylation reaction is performed by using an iridium catalyst including a hitherto reported bipyridyl compound as a ligand, the control of the substitution position of a boron in an aromatic compound is difficult, and a selective borylation at an intended position is not achievable.

Accordingly, the technical problem of the present invention is to provide a compound capable of being a novel ligand allowing regioselective borylation to be performed in the aromatic borylation reaction, and a catalyst using the same compound.

Solution to Problem

Thus, the present inventors made various studies on the ligand enabling regioselective borylation in the aromatic borylation reaction, and consequently succeeded in the synthesis of a novel compound having a bipyridine skeleton and a benzeneureido skeleton. Moreover, when an aromatic borylation reaction was performed by using a catalyst having the aforementioned compound as a ligand, the borylation reaction proceeded selectively at the meta position of the aromatic compound, and thus, the present inventors found that the aforementioned catalyst is useful as a meta-selective borylation catalyst, and consequently accomplished the present invention.

Specifically, the present invention provide the following [1] to [6].

[1] A bipyridyl compound represented by a general formula (1):

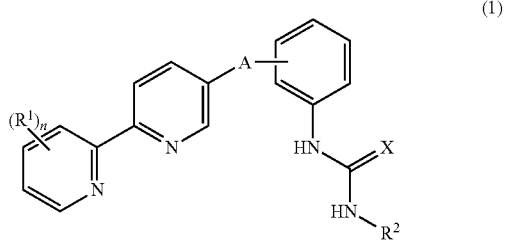

(wherein A represents a single bond, a vinylene group (—CH=CH—) or an ethynylene group (—C≡C—);
X represents an oxygen atom or a sulfur atom;
n pieces of $R^1$ may be the same or different, and $R^1$ represents a hydrogen atom, a halogen atom, an optionally substituted hydrocarbon group, an optionally substituted alkoxy group, an optionally substituted aryloxy group, an optionally substituted amino group, a cyano group, a nitro group, or an alkoxycarbonyl group, or two adjacent $R^1$ may form a saturated or unsaturated ring structure optionally containing a hetero atom together with the carbon atoms bonded to the two $R^1$;
$R^2$ represents a hydrogen atom, an optionally substituted hydrocarbon group, an optionally substituted alkoxy group, or an optionally substituted aryloxy group; and
n represents a number of 1 to 4).

[2] The bipyridyl compound according to [1], wherein A is a single bond.

[3] The bipyridyl compound according to [1] or [2], wherein $R^1$ is a hydrogen atom, a halogen atom, an alkyl group having 1 to 10 carbon atoms, an alkenyl group having 2 to 10 carbon atoms, a cycloalkyl group having 3 to 7 carbon atoms, an aryl group having 6 to 10 carbon atoms, an aryloxy group having 6 to 10 carbon atoms, an alkoxy group having 1 to 10 carbon atoms, a $C_{1-6}$ alkylamino group, a di ($C_{1-6}$ alkyl)amino group or a $C_{1-10}$ alkoxycarbonyl group.

[4] The bipyridyl compound according to any one of [1] to [3], wherein $R^2$ is a hydrogen atom, an optionally substituted alkyl group having 1 to 10 carbon atoms, an optionally substituted alkenyl group having 2 to 10 carbon atoms, an optionally substituted cycloalkyl group having 3 to 7 carbon atoms, an optionally substituted aryl group having 6 to 10 carbon atoms, an optionally substituted alkoxy group having 1 to 10 carbon atoms or an optionally substituted aryloxy group having 6 to 10 carbon atoms.

[5] An aromatic borylation catalyst including the bipyridyl compound according to any one of [1] to [4] as a ligand.

[6] The catalyst according to [5], wherein the bipyridyl compound according to any one of [1] to [4] is coordinated to iridium.

Effects of the Invention

The catalyst including the compound (1) of the present invention as a ligand is useful as a catalyst to selectively introduce a boron atom into the meta position of an aromatic compound. Accordingly, the use of the catalyst including the compound (1) of the present invention as a ligand enables the production of various regioselective aromatic boron compounds usable in the coupling reaction such as the Suzuki-Miyaura reaction.

EMBODIMENTS TO CARRY OUT THE INVENTION

The bipyridyl compound of the general formula (1) is characterized by having both of a bipyridine skeleton and a benzeneureido skeleton.

In the general formula (1), A represents a single bond, a vinylene group or an ethynylene group. Among these, a single bond or an ethynylene group are preferable, and a single bond is more preferable.

The bonding position of A in the benzene ring may be any of the ortho position, meta position and para position in relation to the ureido group, and is more preferably the ortho position.

X represents an oxygen atom or a sulfur atom. Of these, an oxygen atom is preferable.

The n pieces of $R^1$ may be the same or different, and $R^1$ represents a hydrogen atom, a halogen atom, an optionally substituted hydrocarbon group, an optionally substituted alkoxy group, an optionally substituted aryloxy group, an optionally substituted amino group, a cyano group, a nitro group, or an alkoxycarbonyl group, or two adjacent $R^1$ may form a saturated or unsaturated ring structure optionally containing a hetero atom together with the carbon atoms bonded to the two $R^1$.

Examples of the halogen atom include a fluorine atom, a bromine atom, a chlorine atom and an iodine atom.

As a hydrocarbon group, a hydrocarbon group having 1 to 16 carbon atoms is preferable, an alkyl group having 1 to 16 carbon atoms, an alkenyl group having 2 to 16 carbon atoms, a cycloalkyl group having 3 to 16 carbon atoms, an aryl group having 6 to 14 carbon atoms and an arylalkyl group having 7 to 16 carbon atoms are more preferable, and an alkyl group having 1 to 16 carbon atoms, an alkenyl group having 2 to 16 carbon atoms, a cycloalkyl group having 3 to 7 carbon atoms, an aryl group having 6 to 10 carbon atoms and an arylalkyl group having 7 to 16 carbon atoms are furthermore preferable.

Examples of the alkyl group having 1 to 16 carbon atoms include: linear or branched alkyl groups such as a methyl group, an ethyl group, an n-propyl group, an isopropyl group, an n-butyl group, an isobutyl group, a sec-butyl group, a tert-butyl group, an n-pentyl group, an isopentyl group, an n-hexyl group, an n-octyl group and an n-decyl group. Examples of the alkenyl group having 2 to 16 carbon atoms include: a vinyl group, an allyl group, a propenyl group, a butenyl group and a hexenyl group. Examples of the cycloalkyl group having 3 to 7 carbon atoms include: a cyclopropyl group, a cyclobutyl group, a cyclopentyl group, a cyclohexyl group and a cycloheptyl group. Examples of the aryl group having 6 to 10 carbon atoms include a phenyl group and a naphthyl group. Examples of the arylalkyl group having 7 to 16 carbon atoms include a phenyl-$C_{1-6}$ alkyl group and a naphthyl-$C_{1-6}$ alkyl group.

As the alkoxy group, an alkoxy group having 1 to 16 carbon atoms is preferable and an alkoxy group having 1 to 6 carbon atoms is more preferable. Specific examples of the alkoxy group include a methoxy group, an ethoxy group, an n-propyloxy group and an isopropyloxy group. Examples of the aryloxy group include a $C_{6-10}$ aryloxy group, and as the aryloxy group, a phenoxy group, a naphthyloxy group and the like are more preferable.

Examples of the alkoxycarbonyl group include a $C_{1-6}$ alkoxycarbonyl group, and specific examples of the alkoxycarbonyl group include a methoxycarbonyl group and an ethoxycarbonyl group.

Here, examples of the group capable of being substituted in the hydrocarbon group represented by $R^1$ include: 1 to 3 halogen atoms, a cyano group, a nitro group, a halogeno $C_{1-6}$ alkyl group and a $C_{1-6}$ alkoxy group. Examples of the group capable of being substituted in the alkoxy group and the aryloxy group include 1 to 3 halogen atoms, a cyano group, a nitro group, a halogeno $C_{1-6}$ alkyl group and a $C_{1-6}$ alkoxy group. Examples of the group capable of being substituted in the amino group include a $C_{1-6}$ alkyl group and a halogeno $C_{1-6}$ alkyl group.

Here, n represents a number of 1 to 4, and is preferably a number of 1 or 2.

The substitution position of $R^1$ is not particularly limited, but is preferably a position not disturbing the coordination bonding of the nitrogen atom of the pyridine ring to a metal atom, namely, a position distant from the nitrogen atom, preferably a position at the meta position or the para position relative to the nitrogen atom, and particularly preferably the para position.

$R^2$ represents a hydrogen atom, an optionally substituted hydrocarbon group, an optionally substituted alkoxy group, or an optionally substituted aryloxy group.

As the hydrocarbon group, a hydrocarbon group having 1 to 16 carbon atoms is preferable, an alkyl group having 1 to 16 carbon atoms, an alkenyl group having 2 to 16 carbon atoms, a cycloalkyl group having 3 to 16 carbon atoms, an aryl group having 6 to 14 carbon atoms and an arylalkyl group having 7 to 16 carbon atoms are more preferable, and an alkyl group having 1 to 16 carbon atoms, an alkenyl group having 2 to 16 carbon atoms, a cycloalkyl group having 3 to 7 carbon atoms, an aryl group having 6 to 10 carbon atoms and an arylalkyl group having 7 to 16 carbon atoms are furthermore preferable.

Examples of the alkyl group having 1 to 16 carbon atoms include linear or branched alkyl groups such as a methyl group, an ethyl group, an n-propyl group, an isopropyl group, an n-butyl group, an isobutyl group, a sec-butyl group, a tent-butyl group, an n-pentyl group, an isopentyl group, an n-hexyl group, an n-octyl group and an n-decyl group. Examples of the alkenyl group having 2 to 16 carbon atoms include: a vinyl group, an allyl group, a propenyl group, a butenyl group and a hexenyl group. Examples of the cycloalkyl group having 3 to 7 carbon atoms include: a cyclopropyl group, a cyclobutyl group, a cyclopentyl group, a cyclohexyl group and cycloheptyl group. Examples of the aryl group having 6 to 10 carbon atoms include: a phenyl group and a naphthyl group. Examples of the arylalkyl group having 7 to 16 carbon atoms include a phenyl $C_{1-6}$ alkyl group and a naphthyl $C_{1-6}$ alkyl group.

As the alkoxy group, an alkoxy group having 1 to 16 carbon atoms is preferable, and an alkoxy group having 1 to 6 carbon atoms is more preferable. Specific examples of the alkoxy group include: a methoxy group, an ethoxy group, an n-propyloxy group and an isopropyloxy group. Examples of the aryloxy group include a $C_{6-10}$ aryloxy group, and a phenoxy group, a naphthyloxy group and the like are more preferable.

Examples of the group capable of being substituted in the hydrocarbon group represented by $R^2$ include: 1 to 3 halogen atoms, a cyano group, a nitro group, a halogeno $C_{1-6}$ alkyl group and a $C_{1-6}$ alkoxy group. Examples of the group capable of being substituted in an alkoxy group and an aryloxy group include: 1 to 3 halogen atoms, a cyano group, a nitro group, a halogeno $C_{1-6}$ alkyl group and a $C_{1-6}$ alkoxy group.

As $R^1$, a hydrogen atom, a halogen atom, an alkyl group having 1 to 10 carbon atoms, an alkenyl group having 2 to 10 carbon atoms, a cycloalkyl group having 3 to 7 carbon atoms, an aryl group having 6 to 10 carbon atoms, an alkoxy group having 1 to 10 carbon atoms, an aryloxy group having 6 to 10 carbon atoms, a $C_{1-6}$ alkylamino group, a di($C_{1-6}$ alkyl)amino group, a cyano group and a $C_{1-10}$ alkoxycarbonyl group are more preferable.

As $R^2$, a hydrogen atom, an optionally substituted alkyl group having 1 to 10 carbon atoms, an optionally substituted alkenyl group having 2 to 10 carbon atoms, an optionally substituted cycloalkyl group having 3 to 7 carbon atoms, an optionally substituted aryl group having 6 to 10 carbon atoms, an optionally substituted alkoxy group having 1 to 10 carbon atoms and an optionally substituted aryloxy group having 6 to 10 carbon atoms are preferable.

Particularly preferable as $R^2$ are the $C_{1-10}$ alkyl group optionally substituted with the substituent (such as a halogen atom or a $C_{1-6}$ alkoxy group), the $C_{3-7}$ cycloalkyl group optionally substituted with the substituent (such as a $C_{1-6}$ alkyl group, a halogeno $C_{1-6}$ alkyl group or a $C_{1-6}$ alkoxy group), and the phenyl group optionally substituted with the substituent (such as a $C_{1-6}$ alkyl group, a halogeno $C_{1-6}$ alkyl group or a $C_{1-6}$ alkoxy group).

The bipyridyl compound (1) can be produced according to, for example, the following reaction formula.

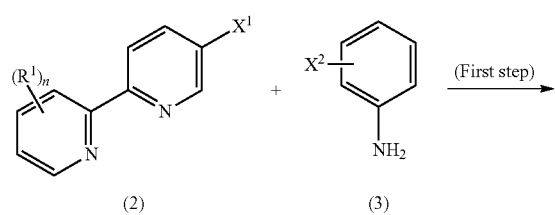

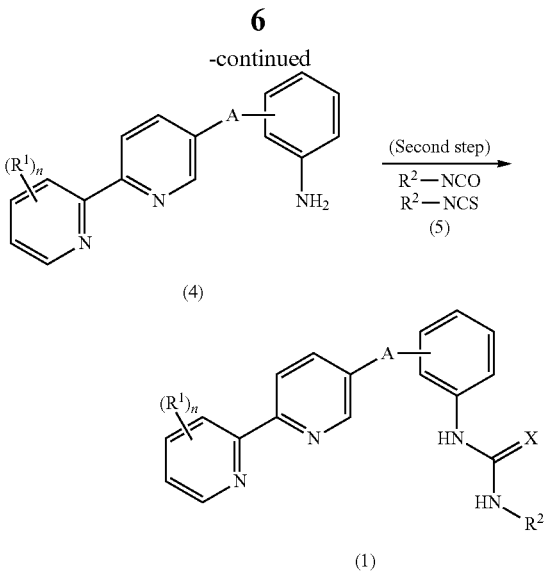

(wherein $X^1$ represents a halogen atom, $X^2$ represents a halogen atom, a vinylene group or an ethynylene group, and $R^1$, A, X, $R^2$ and n are the same as described above).

(First Step)

The first step is a step of obtaining a compound (4) by coupling a bipyridine compound (2) and an aniline compound (3) with each other.

In the case where in the compound (3), $X^2$ is a halogen atom, preferable is the Suzuki-Miyaura coupling in which after the borylation of the compound (3), the compound(3) is coupled with the compound (2). The borylation reaction of the compound (3) can be performed by allowing a boron compound such as pinacolborane to react with the compound (3) in the presence of palladium-phosphine and a base. The subsequent coupling reaction can be performed by adding a base such as barium hydroxide.

As the boron compound, pinacolborane, bis(pinacolato) diborane and the like are used. As palladium-phosphine, for example, bis(diphenylphosphino)alkanes (such as DPPM, DPPE and DPPP), bis(diphosphino)ferrocene (DPPF), bis (diphenylphosphino)binaphthyl (BINAP) and xantphos are used. As the base, tertiary amines such as triethylamine are used.

Examples of the base used in the subsequent coupling reaction include: barium hydroxide, sodium carbonate, potassium carbonate and sodium hydrogen carbonate.

The coupling reaction can be performed in an inert solvent such as dioxane at 50 to 100° C. for 2 to 12 hours.

In the case where in the compound (3), $X^2$ is an ethynylene group, the coupling reaction is preferably performed by the Sonogashira coupling using a palladium catalyst, a copper catalyst and a base.

Examples of the palladium catalyst include: tetrakis(triphenylphosphine)palladium(0) and dichlorobis(triphenylphosphine)palladium(II). As the copper catalyst, copper halides such as copper iodide are preferable. As the base, tertiary amines such as triethylamine are preferable.

The coupling reaction can be performed in an amine at 30 to 100° C. for 1 to 10 hours.

(Second Step)

The second step is a step of obtaining the bipyridyl compound (1) by allowing an isocyanate (5) or a thioisocyanate (5) to react with the compound (4).

This reaction can be performed by allowing an isocyanate (5) or a thioisocyanate (5) to react with the compound (4), in an inert solvent such as dichloromethane, at a temperature from room temperature to 100° C., for 1 to 10 hours.

The bipyridyl compound (1) thus obtained is useful as a ligand of an aromatic borylation catalyst for borylation of an aromatic compound. More specifically, a metal catalyst including the bipyridyl compound (1) as a ligand is useful as a catalyst for selective borylation of the meta position of an aromatic compound, and hence the bipyridyl compound (1) is useful as a ligand of the aromatic borylation catalyst.

The aromatic borylation catalyst of the present invention is a transition metal catalyst in which the two nitrogen atoms in the bipyridine skeleton are coordination bonded to the transition metal (M). Examples of such a transition metal include: iridium (Ir), rhenium (Re), rhodium (Rh), palladium (Pd) and ruthenium (Ru); among these, iridium is more preferable.

In the aromatic borylation catalyst, a compound other than the bipyridyl compound (1) can also be coordinated. Examples of such a ligand include cyclooctadiene (cod).

Such an aromatic borylation catalyst can be formed in a borylation reaction system by adding the bipyridyl compound (1) to, for example, M(OMe) (cod) or M(cod)(Cl).

The aromatic borylation reaction using the aromatic borylation catalyst is described.

An aromatic compound and a boron compound such as pinacolborane or bis(pinacolato)diboron are allowed to react with each other in the presence of the catalyst of the present invention, and thus a boron atom is introduced into the aromatic compound. In this case, the use of a monosubstituted aromatic compound as a raw material results in a selective introduction of a boron atom into the meta position of the monosubstituted aromatic compound. This reaction can be performed by using a boron compound in an amount 0.50 to 10 moles in relation to 1 mole of the aromatic compound, in an inert solvent such as p-xylene, cyclohexane or dioxane, at room temperature to 100° C. for 1 to 24 hours. The amount used of the catalyst can be 1.5 mol % in relation to 1 mole of the aromatic compound. Here, examples of the aromatic compound include an aromatic hydrocarbon having 6 to 50 carbon atoms and an aromatic heterocyclic compound having 5 to 45 carbon atoms. Examples of the substituted aromatic compound to be a substrate of the borylation reaction include: compounds having 1 to 2 substituents in these aromatic hydrocarbons or these aromatic heterocyclic compounds. The substituents in such mono- or disubstituted aromatic compounds are not particularly limited; examples of the substituents include: a halogen atom, an alkyl group, a cyclic alkyl group, a hydroxyl group, an alkoxy group, an amino group, an alkylamino group, a dialkylamino group, an acyl group, a carboxyl group, a carbamoyl group, an N-substituted carbamoyl group, a phosphate group, a phosphine group, a carboxyalkyl group, an alkoxycarbonylalkyl group, a phosphinediamide group, an aromatic hydrocarbon group and an aromatic heterocyclic group.

The aromatic boron compound thus obtained are usable as the raw materials for the coupling reaction such as the Suzuki-Miyaura coupling.

EXAMPLES

Next, the present invention is described in detail with reference to Examples, but the present invention is not limited by these Examples at all.

Example 1

(1) 2-([2,2'-Bipyridin]-5-yl)aniline

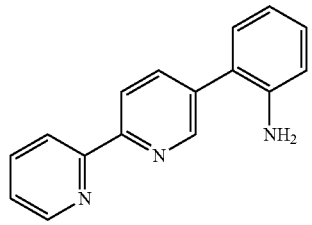 [SMILES: Nc1ccccc1-c1ccc(-c2ccccn2)nc1]

2-Bromoaniline (0.566 mL, 5.00 mmol, 1 equiv) was dissolved in 10 mL of dioxane 10 mL, and to the resulting solution, triethylamine (2.80 mL, 20.0 mmol, 4 equiv), PdCl$_2$ (dppf) (183 mg, 0.250 mmol, 5 mol %) and pinacolborane (2.2 mL, 15.0 mmol, 3 equiv) were added and stirred at 100° C. for 4 hours. The reaction solution was cooled to room temperature, 2.2 mL of water, Ba(OH)$_2$.8H$_2$O (4.73 g, 15.0 mmol, 3 equiv) and 5'-bromo-2,2'-bipyridine (1.08 g, 4.60 mmol, 0.92 equiv) were added to the reaction solution, and then further stirred at 100° C. for 4 hours. The reaction solution was cooled to room temperature, then filtered with Celite, and washed with 120 mL of ethyl acetate. The filtrate was subjected to separatory washing with 120 mL of water, dried with anhydrous sodium sulfate, and then filtered; the solvent was removed under reduced pressure to yield a crude product. By using a silica gel pretreated with a 20% triethylamine-hexane solution (200 mL), the crude product was subjected to a column purification (hexane/ethyl acetate=3/1). Thus, 672 mg (yield: 59%) of a white solid was obtained.

59% yield; white solid; R$_f$=0.50 (hexane/ethyl acetate=1/1); $^1$H NMR (400 MHz, CDCl$_3$) δ3.77 (s, 2H), 6.81 (d, J=7.8 Hz, 1H), 6.88 (d, J=7.5 Hz, 1H), 7.17 (d, J=7.5 Hz, 1H), 7.22 (d, J=7.8 Hz, 1H), 7.33 (dd, J=7.8, 5.2 Hz, 1H), 7.84 (dd, J=7.8, 7.8 Hz, 1H), 7.96 (d, J=8.2 Hz, 1H), 8.43 (d, J=7.8 Hz, 1H), 8.47 (d, J=8.2 Hz, 1H), 8.71 (d, J=5.2 Hz, 1H), 8.80 (s, 1H); $^{13}$C NMR (100 MHz, CDCl$_3$) δ 116.0, 119.0, 121.0, 121.1, 123.6, 123.8, 129.5, 130.6, 135.3, 137.0, 137.5, 143.9, 149.3, 149.5, 154.9, 156.0; IR (KBr, v/cm$^{-1}$) 3346, 3219, 1459, 1357, 1240, 1094, 994, 858, 751, 644; HRMS (ESI$^+$) Calcd for C$_{16}$H$_{13}$N$_3$Na ([M+Na]$^+$) 270.1002, Found 270.1007.

(2) 1-(2-([2,2'-Bipyridin]-5-yl)phenyl)-3-cyclohexylurea

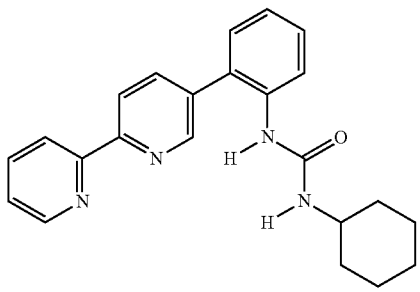

2-([2,2'-Bipyridin]-5-yl)aniline (371 mg, 1.5 mmol, 1.0 equiv), isocyanatecyclohexane (0.29 mL, 2.3 mmol, 1.5 equiv) were dissolved in 5.0 mL of dichloromethane, and stirred at room temperature for 24 hours. The solvent was removed under reduced pressure from the reaction solution to yield a crude product. By recrystallization (hexane/dichloromethane), 281 mg (yield: 50%) of a target product was obtained.

50% yield; white solid; $R_f$=0.53 (hexane/ethyl acetate=1/2); $^1$H NMR (400 MHz, CDCl$_3$) δ0.94-1.10 (m, 3H), 1.27-1.34 (m, 3H), 1.52-1.67 (m, 2H), 1.86-1.89 (m, 2H), 3.51-3.59 (m, 1H), 4.86-4.97 (m, 1H), 6.26-6.35 (m, 1H), 7.21 (dd, J=7.2, 6.3 Hz, 1H), 7.30 (d, J=6.3 Hz, 1H), 7.35 (dd, J=7.2, 7.2 Hz, 1H), 7.42 (d, J=7.2 Hz, 1H), 7.84-7.87 (m, 2H), 7.92 (d, J=8.6 Hz, 1H), 8.39 (d, J=8.0 Hz, 1H), 8.44 (d, J=8.6 Hz, 1H), 8.69-8.71 (m, 2H); $^{13}$C NMR (125 MHz, CDCl$_3$) δ 25.0, 25.6, 33.7, 49.2, 121.1, 121.3, 122.5, 123.8, 124.1, 129.0, 129.6, 130.4, 134.8, 136.6, 137.2, 137.9, 149.4, 149.5, 154.8, 155.1, 155.5; IR (KBr, ν/cm$^{-1}$) 3245, 3219, 1458, 1367, 1240, 1094, 994, 858, 751, 644; HRMS (ESI$^+$)Calcd for C$_{23}$H$_{24}$N$_4$NaO ([M+Na]$^+$) 395.1842, Found 395.1850.

Examples 2 to 8

The following compounds were synthesized in the same manner as Example 1.

Example 2

1-(2-([2,2'-Bipyridin]-5-yl)phenyl)-3-hexylurea

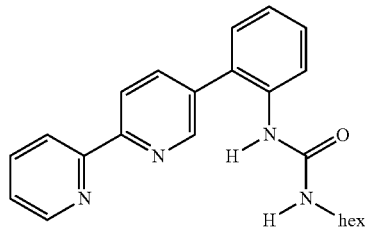

62% yield; white solid; $R_f$=0.32 (hexane/ethyl acetate=1/1); $^1$H NMR (500 MHz, CDCl$_3$) δ 0.79 (t, J=6.9 Hz, 3H), 1.16-1.22 (m, 6H), 1.33-1.38 (m, 2H), 3.14 (td, J=7.2, 7.2 Hz, 2H), 5.48 (brs, 1H), 6.70 (s, 1H), 7.12-7.20 (m, 2H), 7.32 (dd, J=6.3, 4.6, 1.2 Hz, 1H), 7.39 (ddd, J=6.3, 4.8, 1.1 Hz, 1H), 7.69 (ddd, J=8.5, 7.6, 2.2 Hz, 1H), 7.81 (ddd, J=7.7, 7.6, 1.6 Hz, 1H), 8.06 (d, J=8.1 Hz, 1H), 8.15 (d, J=8.5 Hz, 1H), 8.19 (d, J=8.1 Hz, 1H), 8.56 (d, J=2.2 Hz, 1H), 8.64 (dd, J=4.0, 1.1 Hz, 1H); $^{13}$C NMR (125 MHz, CDCl$_3$) δ 14.0, 22.5, 26.6, 30.0, 31.5, 40.2, 120.9, 121.1, 122.3, 123.2, 124.0, 128.4, 129.4, 130.1, 135.1, 136.9, 137.1, 137.1, 149.1, 149.4, 154.3, 155.2, 156.1; IR (KBr, ν/cm$^{-1}$) 3292, 2922, 2855, 1626, 1457, 1371, 1266, 1090, 856, 649; HRMS (ESI$^+$) Calcd for C$_{23}$H$_{26}$N$_4$NaO ([M+Na]$^+$) 397.1999, Found 397.1997.

Example 3

1-(2-([2,2'-Bipyridin]-5-yl)phenyl)-3-(4-methoxyphenyl)urea

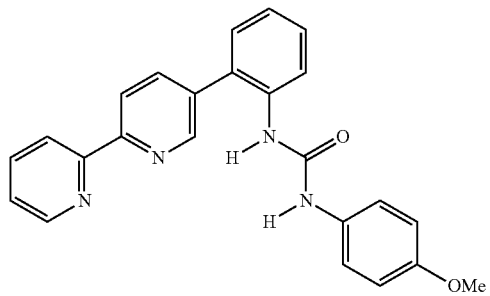 [SMILES: COc1ccc(NC(=O)Nc2ccccc2-c2ccc(-c3ccccn3)nc2)cc1]

6.5% yield; white solid; $R_f$=0.50 (hexane/ethyl acetate=1/2); $^1$H NMR (400 MHz, CDCl$_3$) δ 3.62 (s, 3H), 6.71 (d, J=8.6 Hz, 2H), 6.98 (d, J=8.6 Hz, 2H), 7.20-7.22 (m, 1H), 7.36-7.38 (m, 3H), 7.46-7.49 (m, 1H), 7.54 (s, 1H), 7.81 (dd, J=8.0, 2.0 Hz, 1H), 7.89 (ddd, J=8.0, 7.7, 1.7 Hz, 1H), 7.94-7.96 (m, 1H), 8.44 (d, J=8.0 Hz, 1H), 8.46 (d, J=8.0 Hz, 1H), 8.63 (d, J=1.7 Hz, 1H), 8.73 (d, J=4.6 Hz, 1H); $^{13}$C NMR (125 MHz, DMSO-d$_6$) δ 55.6, 114.1, 120.4, 121.0, 124.7, 126.8, 127.8, 129.2, 130.2, 130.6, 132.0, 135.5, 135.7, 137.1, 137.6, 137.9, 149.3, 149.8, 154.2, 155.3, 157.2, 181.4; IR (KBr, ν/cm$^{-1}$) 3278, 1636, 1509, 1458, 1370, 1244, 1111, 855, 756, 649; HRMS (ESI$^+$) Calcd for C$_{24}$H$_{20}$N$_4$NaO$_2$([M+Na]$^+$) 419.1478, Found 419.1458.

Example 4

1-(2-([2,2'-Bipyridin]-5-yl)phenyl)-3-(4-trifluoromethylphenyl)urea

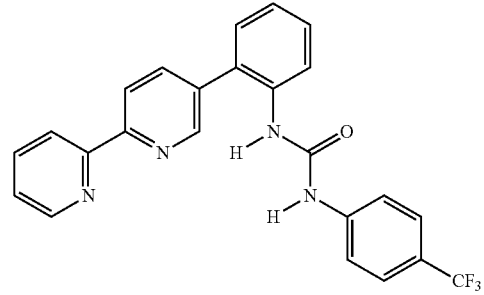 [SMILES: O=C(Nc1ccc(C(F)(F)F)cc1)Nc1ccccc1-c1ccc(-c2ccccn2)nc1]

50% yield; pale yellow solid; $R_f$=0.63 (hexane/ethyl acetate=1/2); $^1$H NMR (400 MHz, CDCl$_3$) δ 7.10-7.16 (m, 2H), 7.35-7.53 (m, 7H), 7.64 (d, J=8.1 Hz, 1H), 7.84-7.85 (m, 2H), 8.22 (brs, 1H), 8.42 (d, J=8.3 Hz, 1H), 8.52 (d, J=1.3 Hz, 1H), 8.57 (d, J=3.1 Hz, 1H), 9.35 (brs, 1H); $^{13}$C NMR (125 MHz, CDCl$_3$) δ 118.1, 118.7, 121.1, 121.3, 123.2, 123.6 (q, J=33.6 Hz), 124.3 (q, J=271 Hz), 124.5, 126.1 (q, J=3.6 Hz), 127.2, 129.9, 130.3, 135.8, 136.9, 137.7, 138.6, 143.0, 149.5, 150.1, 153.2, 153.5; $^{19}$F NMR (368 MHz, CDCl$_3$) δ −63.8 (s, 3F); IR (KBr, ν/cm$^{-1}$) 3331, 3058, 1716, 1654, 1449, 1329, 1165, 1014, 842, 759; HRMS (ESI$^+$) Calcd for C$_{24}$H$_{17}$F$_3$N$_4$NaO ([M+Na]$^+$) 457.1247, Found 457.1252.

Example 5

1-(2-([2,2'-Bipyridin]-5-yl)phenyl)-3-(4-butylphenyl)urea

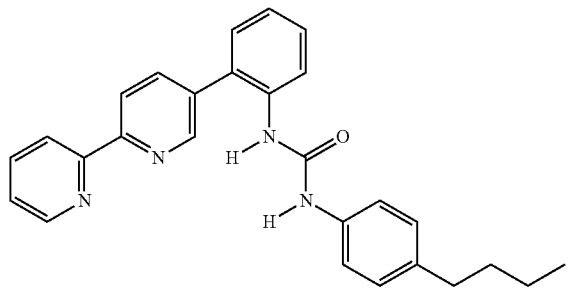 [SMILES: CCCCc1ccc(NC(=O)Nc2ccccc2-c2ccc(-c3ccccn3)nc2)cc1]

276 yield; white solid; $R_f$=0.64 (hexane/ethyl acetate=1/2); $^1$H NMR (400 MHz, CDCl$_3$) δ 0.85 (t, J=7.5 Hz, 3H), 1.20-1.28 (m, 2H), 1.38-1.46 (m, 2H), 2.38 (t, J=7.7 Hz, 2H), 6.94 (d, J=1.9 Hz, 2H), 7.05-7.15 (m, 4H), 7.34 (dd, J=7.2, 4.9 Hz, 1H), 7.41 (ddd, J=7.7, 7.7, 1.7 Hz, 1H), 7.59 (d, J=8.0 Hz, 1H), 7.82 (dd, J=7.2, 7.2 Hz, 1H), 8.01-8.03 (m, 1H), 8.15-8.16 (m, 1H), 8.30 (d, J=8.6 Hz, 1H), 8.52 (s, 1H), 8.65 (d, J=4.6 Hz, 1H); $^{13}$C NMR (125 MHz, CDCl$_3$) δ 14.0, 22.4, 33.7, 35.0, 120.6, 121.0, 121.3, 121.4, 123.2, 124.2, 127.8, 129.0, 129.6, 130.2, 135.1, 136.2, 136.8, 137.3, 138.1, 138.3, 149.4, 149.7, 153.6, 154.4, 155.0; IR (KBr, v/cm$^{-1}$) 3293, 1637, 1546, 1509, 1458, 1372, 1246, 1122, 799, 757; HRMS (ESI$^+$) Calcd for C$_{27}$H$_{26}$N$_4$NaO ([M+Na]$^+$) 445.1999, Found 445.1989.

Example 6

1-(2-([2,2'-Bipyridin]-5-yl)phenyl)-3-(2,6-dimethylphenyl)urea

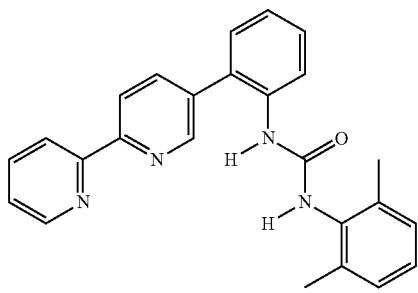 [SMILES: Cc1cccc(C)c1NC(=O)Nc1ccccc1-c1ccc(-c2ccccn2)nc1]

58% yield; white solid; $R_f$=0.30 (hexane/ethyl acetate=1/1); $^1$H NMR (400 MHz, CDCl$_3$) δ 2.15 (s, 6H), 5.73 (s, 1H), 6.19 (s, 1H), 6.78-6.80 (m, 1H), 6.84 (d, J=6.7 Hz, 2H), 7.13-7.18 (m, 2H), 7.36-7.44 (m, 2H), 7.48 (d, J=7.6 Hz, 1H), 7.89 (ddd, J=7.6, 7.6, 1.8 Hz, 1H), 8.23 (d, J=8.1 Hz, 1H), 8.29 (d, J=8.5 Hz, 1H), 8.39 (s, 1H), 8.43 (d, J=8.1 Hz, 1H), 8.75 (d, J=4.9 Hz, 1H); $^{13}$C NMR (125 MHz, CDCl$_3$) δ 18.3, 120.9, 121.1, 124.1, 128.4, 128.5, 129.0, 129.6, 130.0, 132.8, 133.8, 136.1, 137.0, 137.1, 137.3, 149.1, 149.5, 154.1, 155.3, 155.6, 155.7, 157.0; IR (KBr, v/cm$^{-1}$) 3265, 1632, 1550, 1457, 1371, 1240, 1002, 855, 797, 717; HRMS Calcd for C$_{25}$H$_{22}$N$_4$NaO ([M+Na]$^+$) 417.1686, Found 417.1679.

Example 7

1-(2-([2,2'-Bipyridin]-5-yl)phenyl)-3-cyclohexylthiourea

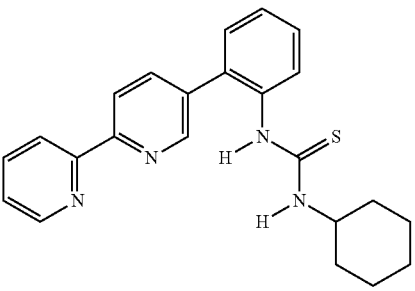 [SMILES: S=C(Nc1ccccc1-c1ccc(-c2ccccn2)nc1)NC1CCCCC1]

51% yield; white solid; $R_f$=0.36 (hexane/ethyl acetate=1/1); $^1$H NMR (400 MHz, CDCl$_3$) δ 0.96-1.12 (m, 3H), 1.24-1.37 (m, 2H), 1.55-1.63 (m, 4H), 1.90-1.93 (m, 2H), 4.14 (s, 1H), 5.71 (s, 1H), 7.30-7.34 (m, 2H), 7.41-7.54 (m, 3H), 7.82 (d, J=8.1 Hz, 1H), 7.85 (ddd, J=8.1, 8.1, 2.2 Hz, 1H), 8.40 (d, J=8.1 Hz, 1H), 8.47 (d, J=9.0 Hz, 1H), 8.68-8.73 (m, 2H); $^{13}$C NMR (100 MHz, CDCl$_3$) δ 24.8, 25.5, 32.7, 54.1, 121.1, 121.4, 124.0, 127.9 (2C), 128.6, 130.0, 131.6, 133.6, 135.3, 137.0 (2C), 148.9, 149.4, 155.7, 155.8, 179.5; IR (KBr, v/cm$^{-1}$) 3293, 2931, 2857, 1637, 1458, 1373, 1229, 1001, 841, 656; HRMS (ESI$^+$) Calcd for C$_{23}$H$_{24}$N$_4$NaS ([M+Na]$^+$) 411.1619, Found 411.1611.

Example 8

(1) 2-([2,2'-Bipyridin]-5-ylethynyl)aniline

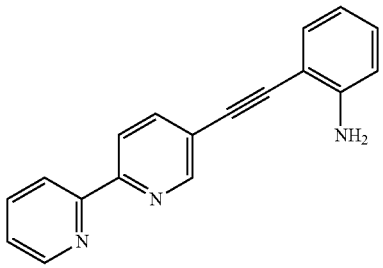 [SMILES: Nc1ccccc1C#Cc1ccc(-c2ccccn2)nc1]

A triethylamine (1.3 mL) solution of PdCl$_2$(PPh$_3$)$_2$ (1.8 mg, 2.5 μmol, 0.5 mol %), CuI (1.0 mg, 5.0 μmol, 1.0 mol %) and 5-bromo-2,2'-bipyridine (118 mg, 0.50 mmol, 1 equiv) was stirred for 15 minutes at room temperature. To the resulting solution, 2-ethylaniline (93 μL, 0.6 mmol, 1.2 equiv) was added, and then stirred at 70° C. for 3.5 hours. The temperature of the solution was cooled to room temperature, then the solid substances were removed by filtration with Celite, and the obtained filtrate was washed with water (20 mL) and was subjected to extraction with diethyl ether (3×20 mL). The crude product was isolated and purified by silica gel column chromatography (hexane/ethyl acetate=3/1), and thus 106 mg (yield: 78%) of a target product was obtained as a white solid.

78% yield; white solid; $R_f$=0.15 (hexane/ethyl acetate=3/1); $^1$H NMR (400 MHz, CDCl$_3$) δ 4.32 (brs, 2H), 6.72-6.77 (m, 2H), 7.18 (dt, J=7.6, 1.3 Hz, 1H), 7.34 (dd, J=7.6, 4.9 Hz, 1H), 7.40 (dd, J=8.1, 1.8 Hz, 1H), 7.84 (dd, J=7.6, 7.6

Hz, 1H), 7.93 (dd, J=8.1, 2.2 Hz, 1H), 8.41-8.44 (m, 2H), 8.70 (d, J=4.0 Hz, 1H), 8.81 (dd, J=8.2, 1.8 Hz, 1H); $^{13}$C NMR (125 MHz, CDCl$_3$) δ 90.4, 91.8, 107.3, 114.6, 118.2, 120.5 (2C), 121.5, 124.0, 130.4, 132.5, 137.1, 139.2, 148.1, 149.4, 151.5, 154.9, 155.6; IR (KBr, v/cm$^{-1}$) 3313, 2362, 2206, 1624, 1569, 1488, 1459, 1312, 1093, 739; HRMS (ESI$^+$) Calcd for C$_{18}$H$_{13}$N$_3$Na ([M+Na]$^+$) 294.1007, Found 294.0999.

(2) 1-(2-([2,2T-Bipyridin]-5-ylethynyl)phenyl)-3-phenylurea

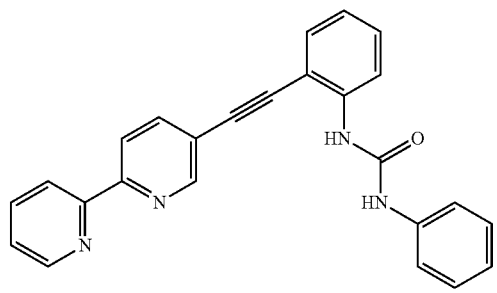 [SMILES: O=C(Nc1ccccc1)Nc1ccccc1C#Cc1ccc(-c2ccccn2)nc1]

The target product was produced in the same manner as Example 1 (2).

46% yield; white solid; R$_f$=0.29 (ethyl acetate); $^1$H NMR (500 MHz, CDCl$_3$) δ 6.49 (brs, 1H), 7.04-7.10 (m, 3H), 7.29-7.30 (m, 1H), 7.34-7.41 (m, 4H), 7.47-7.49 (m, 2H), 7.58 (d, J=6.3 Hz, 1H), 7.86 (dd, J=5.8, 5.8 Hz, 1H), 8.30 (d, J=6.7 Hz, 1H), 8.37 (d, J=10.2 Hz, 1H), 8.44 (d, J=6.3 Hz, 1H), 8.56 (s, 1H), 8.72 (d, J=3.6 Hz, 1H); $^{13}$C NMR (125 MHz, CDCl$_3$) δ 88.8, 92.7, 111.4, 119.4, 134.4, 120.4, 121.6, 122.8, 123.4, 124.3, 125.7, 127.7, 129.8, 130.5, 132.2, 137.2, 139.5, 139.9, 149.5, 151.7, 153.0, 155.3, 155.4; IR (KBr, v/cm$^{-1}$) 3299, 1644, 1576, 1552, 1458, 1296, 1091, 794, 743, 692; HRMS (ESI$^+$) Calcd for C$_{25}$H$_{18}$N$_4$NaO ([M+Na]$^+$) 413.1378, Found 413.1388.

Example 9

(1) Meta-selective Borylation of an Aromatic Compound With an Iridium Catalyst

In a dried test tube, to a p-xylene (1.5 mL) solution of N,N-dihexylbenzamide (72.4 mg, 0.250 mmol, 1.00 equiv), [Ir(OMe)(cod)]$_2$ (1.2 mg, 1.9 μmol, 0.75 mol %), 1-(2-([2, 2'-bipyridin]-5-yl)phenyl)-3-cyclohexylurea (1.2 mg, 3.8 μmol, 1.5 mol %) and bis(pinacolato)diboron (47.6 mg, 0.188 mmol, 0.750 equiv) were added and stirred at 25° C. for 24 hours. The solvent was removed under reduced pressure, and then the products were isolated and prepared by recycling preparative HPLC.

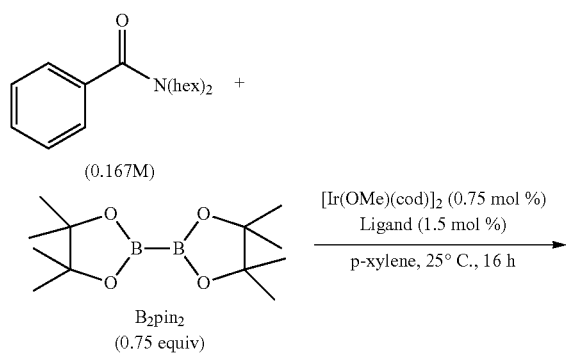

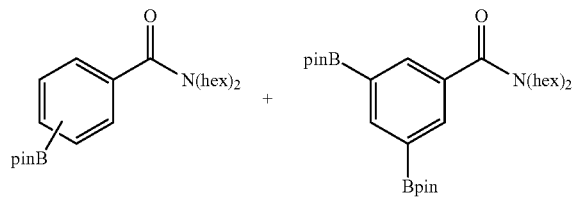

The obtained compounds were as follows.

N,N-Dihexyl-3-(4,4,5,5-tetramethyl-1,3,2-dioxaborolan-2-yl)benzamide

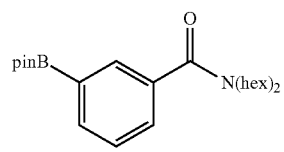

40% yield; colorless oil; $^1$H NMR (500 M Hz, CDCl$_3$) δ 0.82 (t, J=6.9 Hz, 3H), 0.89-0.92 (m, 3H), 1.10-1.21 (m, 6H), 1.30-1.41 (m, 18H), 1.46-1.50 (m, 2H), 1.65-1.66 (m, 2H), 3.15 (t, J=6.9 Hz, 2H), 3.46 (t, J=7.2 Hz, 2H), 7.38 (dd, J=8.0, 7.2 Hz, 1H), 7.43 (ddd, J=8.0, 1.7, 1.7 Hz, 1H), 7.78 (s, 1H), 7.80 (ddd, J=7.2, 1.7, 1.7 Hz, 1H); $^{13}$C NMR (100 MHz, CDCl$_3$) δ 14.1, 14.2, 22.6, 22.8, 25.0, 26.3, 26.9, 27.6, 28.8, 31.4, 31.8, 45.0, 49.2, 84.1, 127.8, 129.3, 132.7, 135.4, 136.8, 171.8; $^{11}$B NMR (130 MHz, CDCl$_3$) δ 30.2; IR (neat, v/cm$^{-1}$) 2930, 2858, 1626, 1411, 1358, 1319, 1144, 861, 754, 666; HRMS (ESI$^+$) Calcd for C$_{25}$H$_{42}$BNNaO$_3$([M+Na]$^+$) 438.3150, Found 438.3151.

N,N-Dihexyl-4-(4,4,5,5-tetramethyl-1,3,2-dioxaborolan-2-yl)benzamide

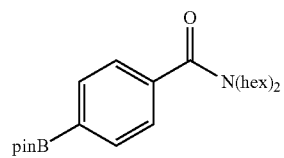

3.3o yield; colorless oil; $^1$H NMR (500MHz, CDCl$_3$) δ 0.82 (t, J=7.2 Hz, 3H), 0.89-0.92 (m, 3H), 1.06-1.11 (m, 4H), 1.18-1.25 (m, 2H), 1.35-1.36 (m, 18H), 1.46-1.47 (m, 2H), 1.63-1.66 (m, 2H), 3.13 (t, J=6.9 Hz, 2H), 3.46 (t, J=7.2 Hz, 2H), 7.32 (d, J=8.3 Hz, 2H), 7.81 (d, J=8.3 Hz, 2H); $^{13}$C NMR (125 MHz, CDCl$_3$) δ 14.0, 14.1, 22.5, 22.7, 25.0, 26.3, 26.8, 27.6, 28.7, 31.4, 31.7, 44.8, 49.0, 84.1, 125.7, 134.8, 140.1, 171.6; $^{11}$B NMR (130 MHz, CDCl$_3$) δ 29.9; IR (neat, v/cm$^{-1}$) 2929, 1636, 1511, 1396, 1360, 1322, 1144, 1108, 859, 659; HRMS (ESI$^+$) Calcd for C$_{25}$H$_{42}$BNNaO$_3$ ([M+Na]$^+$) 438.3150, Found 438.3170.

N,N-Dihexyl-3,5-bis(4,4,5,5-tetramethyl-1,3,2-di-oxaborolan-2-yl)benzamide

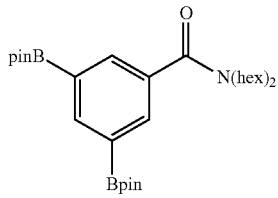

3.0% yield; colorless oil; $^1$H NMR (500 MHz, CDCl$_3$) δ 0.81 (t, J=7.2 Hz, 3H), 0.90-0.93 (m, 3H), 1.10-1.27 (m, 10H), 1.31-1.35 (m, 28H), 1.62-1.66 (m, 2H), 3.12 (t, J=6.9 Hz, 2H), 3.44 (t, J=7.2 Hz, 2H), 7.88 (s 2H), 8.26 (s, 1H); $^{13}$C NMR (100 MHz, CDCl$_3$) δ 14.1, 14.2, 22.5, 22.8, 25.0, 26.3, 27.0, 27.7, 28.9, 31.4, 31.8, 45.0, 49.3, 84.0, 135.5, 136.3, 141.7, 171.7; $^{11}$B NMR (130 MHz, CDCl$_3$) δ 32.9; IR (neat, ν/cm$^-$) 2929, 1628, 1329, 1265, 1142, 967, 889, 801, 755, 718; HRMS (ESI$^+$) Calcd for C$_{31}$H$_{53}$B$_2$NNaO$_5$([M+Na]$^+$) 564.4002, Found 564.4021.

By using the ligand used in (1), the following compounds ((2) to (27)) were obtained in the same manner as the method of (1).

(2) N,N-Dihexyl-2-methoxy-5-(4,4,5,5-tetramethyl-1,3,2-dioxaborolan-2-yl)benzamide and N,N-dihexyl-2-methoxy-4-(4,4,5,5-tetramethyl-1,3,2-dioxaborolan-2-yl)benzamide

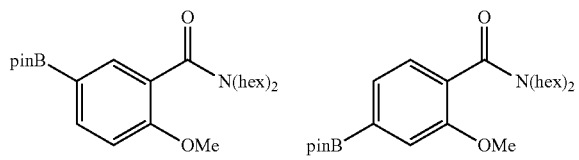

63% yield [meta/para=7.5]; colorless oil; $^{11}$B NMR (130 MHz, CDCl$_3$) δ 31.9; IR (neat, ν/cm$^{-1}$) 2930, 1627, 1410, 1355, 1140, 1027, 965, 851, 754, 683; HRMS (ESI$^+$) Calcd for C$_{26}$H$_{44}$BNNaO$_4$([M+Na]$^+$) 468.3256, Found 468.3246.

N,N-Dihexyl-2-methoxy-5-(4,4,5,5-tetramethyl-1,3,2-dioxaborolan-2-yl)benzamide: $^1$H NMR (400 MHz, CDCl$_3$) δ 0.80 (t, J=7.4 Hz, 3H), 0.91 (t, J=6.7 Hz, 3H), 1.06-1.08 (m, 4H), 1.16-1.50 (m, 22H), 1.62-1.64 (m, 2H), 3.01-3.04 (m, 2H), 3.48-3.49 (m, 2H), 3.82 (s, 3H), 6.87 (d, J=8.3 Hz, 1H), 7.63 (s, 1H), 7.76 (d, J=8.3 Hz, 1H); $^{13}$C NMR (125 MHz, CDCl$_3$) δ 14.1, 14.2, 22.5, 22.8, 24.7, 26.3, 26.7, 27.6, 28.4, 31.4, 31.8, 44.4, 48.5, 55.4, 83.7, 110.1, 126.6, 134.4, 137.0, 157.8, 169.2.

N,N-Dihexyl-2-methoxy-4-(4,4,5,5-tetramethyl-1,3,2-dioxaborolan-2-yl)benzamide: $^1$H NMR (400 MHz, CDCl$_3$) δ 0.80 (t, J=7.4 Hz, 3H), 0.91 (t, J=6.7 Hz, 3H), 1.06-1.08 (m, 4H), 1.18-1.50 (m, 20H), 1.62-1.64 (m, 4H), 3.01-3.04 (m, 2H), 3.48-3.49 (m, 2H), 3.85 (s, 3H), 7.17 (d, J=7.2 Hz, 1H), 7.29 (s, 1H), 7.41 (d, J=7.2 Hz, 1H); $^{13}$C NMR (125 MHz, CDCl$_3$) δ 14.1, 14.2, 22.6, 22.8, 25.0, 26.3, 26.8, 27.5, 28.4, 31.4, 31.8, 44.3, 48.3, 55.6, 84.1, 116.4, 127.1, 127.4, 130.0, 154.6, 169.2.

(3) N,N-Dihexyl-2-methyl-5-(4,4,5,5-tetramethyl-1,3,2-dioxaborolan-2-yl)benzamide and N,N-dihexyl-2-methyl-4-(4,4,5,5-tetramethyl-1,3,2-dioxaborolan-2-yl)benzamide

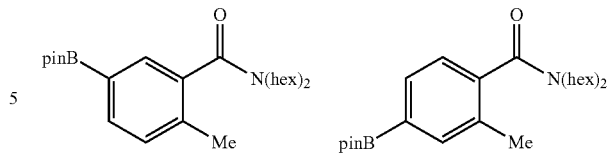

39% yield [meta/para=15]; colorless oil; IR (neat, ν/cm$^{-1}$) 2929, 1634, 1466, 1357, 1145, 1105, 965, 862, 754, 686; HRMS (ESI$^+$) Calcd for C$_{26}$H$_{44}$BNNaO$_3$ ([M+Na]$^+$) 452.3306, Found 452.3306.

N,N-Dihexyl-2-methyl-5-(4,4,5,5-tetramethyl-1,3,2-dioxaborolan-2-yl)benzamide: $^1$H NMR (500 MHz, CDCl$_3$) δ 0.82 (t, J=7.2 Hz, 3H), 0.91 (t, J=6.9 Hz, 3H), 1.07-1.11 (m, 4H), 1.14-1.21 (m, 2H), 1.25-1.39 (m, 18H), 1.41-1.47 (m, 2H), 1.62-1.70 (m, 2H), 2.29 (s, 3H), 3.01-3.05 (m, 2H), 3.39-3.56 (m, 2H), 7.19 (d, J=7.5 Hz, 1H), 7.59 (s, 1H), 7.67 (d, J=7.5 Hz, 1H); $^{13}$C NMR (125 MHz, CDCl$_3$) δ 14.1, 14.2, 19.4, 22.5, 22.8, 25.0, 26.3, 27.0, 27.7, 28.5, 31.3, 31.8, 44.6, 48.6, 83.9, 129.8, 132.3, 134.9, 136.8, 137.4, 171.3; $^{11}$13 NMR (130 MHz, CDCl$_3$) δ 30.5;

N,N-Dihexyl-2-methyl-4-(4,4,5,5-tetramethyl-1,3,2-dioxaborolan-2-yl)benzamide: $^1$H NMR (500 MHz, CDCl$_3$) δ 0.81 (t, J=7.2 Hz, 3H), 0.90 (t, J=6.0 Hz, 3H), 1.04-1.11 (m, 4H), 1.14-1.26 (m, 2H), 1.28-1.47 (m, 20H), 1.62-1.67 (m, 2H), 2.27 (s, 3H), 2.85-3.15 (m, 2H), 3.20-3.75 (m, 2H), 7.14 (d, J=7.8 Hz, 1H), 7.62 (d, J=7.8 Hz, 1H), 7.64 (s, 1H); $^{13}$C NMR (125 MHz, CDCl$_3$) δ 14.1, 14.2, 18.9, 22.6, 22.8, 25.0, 26.4, 27.0, 27.6, 28.5, 31.4, 31.8, 44.4, 48.4, 84.1, 125.3, 132.2, 133.2, 136.7, 140.1, 171.2; $^{11}$B NMR (130 MHz, CDCl$_3$) δ 31.3.

(4) 2-Bromo-N,N-dihexyl-5-(4,4,5,5-tetramethyl-1,3,2-dioxaborolan-2-yl)benzamide and 2-bromo-N,N-dihexyl-4-(4,4,5,5-tetramethyl-1,3,2-dioxaborolan-2-yl)benzamide

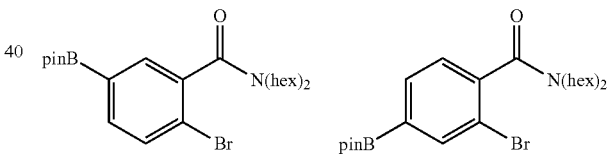

91% yield [meta/para=8.6]; colorless oil; $^{11}$B NMR (130 MHz, CDCl$_3$) δ 30.0; IR (neat, ν/cm$^{-1}$) 2929, 1640, 1590, 1355, 1144, 1094, 964, 839, 754, 688; HRMS (ESI$^+$) Calcd for C$_{25}$H$_{41}$BBrNNaO$_3$ ([M+Na]$^+$) 516.2255, Found 516.2245.

2-Bromo-N,N-dihexyl-5-(4,4,5,5-tetramethyl-1,3,2-dioxaborolan-2-yl)benzamide: $^1$H NMR (400 MHz, CDCl$_3$) δ 0.80 (t, J=7.2 Hz, 3H), 0.91 (t, J=6.7 Hz, 3H), 1.07-1.10 (m, 4H), 1.16-1.20 (m, 2H), 1.32-1.34 (m, 16H), 1.45-1.59 (m, 4H), 1.66-1.68 (m, 2H), 3.01-3.08 (m, 2H), 3.22-3.29 (m, 1H), 3.66-3.73 (m, 1H), 7.55 (d, J=7.9 Hz, 1H), 7.61 (dd, J=7.9, 1.4 Hz, 1H), 7.67 (d, J=1.4 Hz, 1H); $^{13}$C NMR (125 MHz, CDCl$_3$) δ 14.0, 14.2, 22.4, 22.7, 24.8 (br), 26.2, 26.9, 27.3, 28.3, 31.3, 31.7, 44.6, 48.3, 84.2, 122.8, 132.1, 134.2, 135.9, 138.4, 168.9.

2-Bromo-N,N-dihexyl-4-(4,4,5,5-tetramethyl-1,3,2-dioxaborolan-2-yl)benzamide: $^1$H NMR (400 MHz, CDCl$_3$) δ 0.80 (t, J=7.2 Hz, 3H), 0.91 (t, J=6.7 Hz, 3H), 1.07-1.10 (m, 4H), 1.16-1.20 (m, 2H), 1.32-1.34 (m, 16H), 1.45-1.59 (m, 4H), 1.66-1.68 (brs, 2H), 3.01-3.08 (m, 2H), 3.22-3.29 (m, 1H), 3.66-3.73 (m, 1H), 7.23 (d, J=7.4 Hz, 1H), 7.73 (d, J=7.4 Hz, 1H), 7.98 (s, 1H); $^{13}$C NMR (125 MHz, CDCl$_3$)

δ 14.0, 14.2, 22.5, 22.7, 24.9 (br), 26.3, 26.9, 27.2, 28.3, 31.2, 31.7, 44.7, 48.5, 84.4, 119.1, 127.3, 133.6, 138.7, 141.3, 168.8.

(5) 2-Chloro-N,N-dihexyl-5-(4,4,5,5-tetramethyl-1,3,2-dioxaborolan-2-yl)benzamide and 2-chloro-N,N-dihexyl-4-(4,4,5,5-tetramethyl-1,3,2-dioxaborolan-2-yl)benzamide

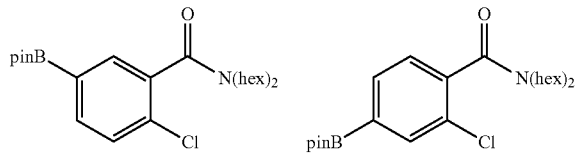

84% yield [meta/para=12]; pale yellow oil; HRMS (ESI+) Calcd for $C_{25}H_{41}BClNNaO_3$ ([M+Na]+) 472.2760, Found 472.2764.

2-Chloro-N,N-dihexyl-5-(4,4,5,5-tetramethyl-1,3,2-dioxaborolan-2-yl)benzamide: $^1$H NMR (400 MHz, CDCl$_3$) δ 0.80 (t, J=7.2 Hz, 3H), 0.91 (t, J=6.7 Hz, 3H), 1.08-1.19 (m, 6H), 1.25-1.61 (m, 20H), 1.63-1.69 (m, 2H), 2.98-3.12 (m, 2H), 3.28-3.34 (m, 1H), 3.64-3.70 (m, 1H), 7.36 (d, J=8.5 Hz, 1H), 7.69 (s, 1H), 7.70 (d, J=8.5 Hz, 1H); $^{13}$C NMR (125 MHz, CDCl$_3$) δ 14.1, 14.2, 22.5, 22.8, 24.8, 26.3, 26.9, 27.4, 28.4, 31.3, 31.8, 44.7, 48.5, 84.3, 129.0, 133.5, 134.3, 136.0, 136.4, 168.2; $^{11}$B NMR (130 MHz, CDCl$_3$) δ 32.1; IR (neat, v/cm$^{-1}$) 2929, 2857, 1645, 1507, 1456, 1387, 1144, 1095, 963, 732.

2-Chloro-N,N-dihexyl-4-(4,4,5,5-tetramethyl-1,3,2-dioxaborolan-2-yl)benzamide: $^1$H NMR (400 MHz, CDCl$_3$) δ 0.81 (t, J=7.2 Hz, 3H), 0.90 (t, J=6.5 Hz, 3H), 1.07-1.20 (m, 6H), 1.25-1.51 (m, 20H), 1.65-1.67 (m, 2H), 2.98-3.12 (m, 2H), 3.19-3.26 (m, 1H), 3.71-3.79 (m, 1H), 7.25 (d, J=7.6 Hz, 1H), 7.69 (d, J=7.6 Hz, 1H), 7.80 (s, 1H); $^{13}$C NMR (125 MHz, CDCl$_3$) δ 14.1, 14.2, 22.5, 22.8, 25.0, 26.4, 26.9, 27.3, 28.4, 31.4, 31.8, 44.6, 48.5, 84.3, 127.4, 132.2, 133.1, 135.7, 139.3, 168.1; $^1$B NMR (130 MHz, CDCl$_3$) 8 30.2; IR (neat, v/cm$^{-1}$) 2929, 2857, 1644, 1498, 1456, 1355, 1143, 1096, 1047, 686.

(6) N,N-Dihexyl-5-(4,4,5,5-tetramethyl-1,3,2-dioxaborolan-2-yl)-2-(trifluoromethyl)benzamide

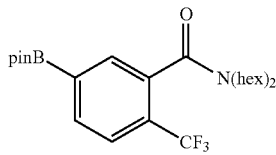

93% yield; colorless oil; $^1$NMR (500 MHz, CDCl$_3$) δ 0.80 (t, J=7.2 Hz, 3H), 0.91 (t, J=6.7 Hz, 3H), 1.07-1.22 (m, 6H), 1.33-1.49 (m, 20H), 1.64-1.65 (m, 2H), 2.88-3.04 (m, 2H), 3.13-3.23 (m, 1H), 3.69-3.79 (m, 1H), 7.65 (d, J=7.9 Hz, 1H), 7.75 (s, 1H), 7.88 (d, J=7.9 Hz, 1H); $^{13}$C NMR (100 MHz, CDCl$_3$) δ 14.0, 14.1, 22.4, 22.7, 24.9, 26.2, 26.8, 27.0, 28.0, 31.3, 31.7, 44.5, 48.8, 84.5, 123.8 (q, J=275 Hz), 125.6 (q, J=4.8 Hz), 127.1, 128.7 (q, J=31.2 Hz), 133.8, 134.9, 168.6; $^{19}$F NMR (368 MHz, CDCl$_3$) δ −62.0; $^{11}$B NMR (130 MHz, CDCl$_3$) δ 30.5; IR (neat, v/cm$^{-1}$) 2930, 2859, 1644, 1505, 1467, 1312, 1102, 1041, 844, 690; HRMS (ESI+) Calcd for $C_{26}H_{41}BF_3NNaO_3$([M+Na]+) 506.3024, Found 506.3018.

(7) N,N-Dihexyl-5-(4,4,5,5-tetramethyl-1,3,2-dioxaborolan-2-yl)-2-(trifluoromethoxy)benzamide and N,N-dihexyl-4-(4,4,5,5-tetramethyl-1,3,2-dioxaborolan-2-yl)-2-(trifluoromethoxy)benzamide

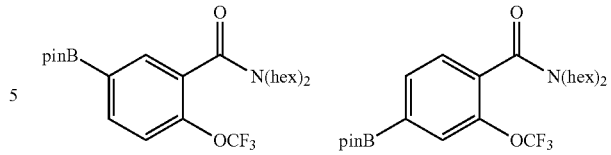

92% yield [meta/para=6.8]; colorless oil; $^{19}$F NMR (368 MHz, CDCl$_3$) δ −58.6; $^{11}$B NMR (130 MHz, CDCl$_3$) δ 30.2; IR (neat, v/cm$^{-1}$) 2931, 2859, 1644, 1468, 1359, 1255, 1003, 965, 850, 687; HRMS (ESI+) Calcd for $C_{26}H_{41}BF_3NNaO_4$ ([M+Na]+) 522.2973, Found 522.2996.

N,N-Dihexyl-5-(4,4,5,5-tetramethyl-1,3,2-dioxaborolan-2-yl)-2-(trifluoromethoxy)benzamide: $^1$NMR (400 MHz, CDCl$_3$) δ 0.80 (t, J=7.2 Hz, 3H), 0.90 (t, J=6.7 Hz, 3H), 1.08-1.09 (m, 4H), 1.17-1.20 (m, 2H), 1.32-1.45 (m, 20H), 1.62-1.67 (m, 2H), 3.04 (t, J=7.6 Hz, 2H), 3.19-3.26 (m, 1H), 3.72-3.76 (m, 1H), 7.25 (d, J=8.3 Hz, 1H), 7.75 (s, 1H), 7.82 (d, J=8.3 Hz, 1H); $^{13}$C NMR (100 MHz, CDCl$_3$) δ 13.9, 14.1, 22.4, 22.6, 24.9, 26.2, 26.7, 27.2, 28.3, 31.2, 31.7, 44.4, 48.4, 84.3, 118.6 (q, J=1.9 Hz), 123.8 (q, J=258 Hz), 129.8, 135.2, 136.7, 147.1 (q, J=1.9 Hz), 166.8.

N,N-Dihexyl-4-(4,4,5,5-tetramethyl-1,3,2-dioxaborolan-2-yl)-2-(trifluoromethoxy)benzamide: $^1$H NMR (400 MHz, CDCl$_3$) δ 0.80 (t, J=7.2 Hz, 3H), 0.90 (t, J=6.7 Hz, 3H), 1.08-1.09 (m, 4H), 1.17-1.20 (m, 2H), 1.32-1.45 (m, 20H), 1.62-1.67 (m, 2H), 3.04 (t, J=7.6 Hz, 2H), 3.19-3.26 (m, 1H), 3.72-3.76 (m, 1H), 7.33 (d, J=7.4 Hz, 1H), 7.67 (s, 1H), 7.73 (d, J=7.4 Hz, 1H); $^{13}$C NMR (100 MHz, CDCl$_3$) 813.9, 14.1, 22.5, 22.6, 24.8, 26.2, 26.7, 27.2, 28.3, 31.3, 31.7, 44.4, 48.3, 84.4, 123.8 (q, J=258 Hz), 125.9, 127.9, 133.2, 133.3, 144.5 (q, J=1.9 Hz), 166.7.

(8) Methyl 2-(dihexylcarbamoyl)-4-(4,4,5,5-tetramethyl-1,3,2-dioxaborolan-2-yl)benzoate

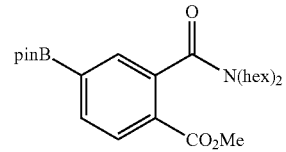

96% yield; pale yellow oil; $^1$H NMR (400 MHz, CDCl$_3$) δ 0.79 (t, J=7.2 Hz, 3H), 0.91 (t, J=7.0 Hz, 3H), 1.05-1.07 (m, 4H), 1.15-1.20 (m, 2H), 1.30-1.47 (m, 20H), 1.69-1.72 (m, 2H), 2.99 (t, J=7.8 Hz, 2H), 3.45-3.49 (m, 2H), 3.86 (s, 3H), 7.70 (d, J=1.0 Hz, 1H), 7.83 (dd, J=8.0, 1.0 Hz, 1H), 7.99 (d, J=8.0 Hz, 1H); $^{13}$C NMR (100 MHz, CDCl$_3$) 813.9, 14.1, 22.3, 22.7, 24.8, 26.2, 26.9, 27.1, 28.0, 31.2, 31.7, 44.8, 48.8, 52.2, 84.3, 129.1, 129.6, 133.4, 134.5, 138.3, 166.2, 170.6; $^{11}$B NMR (130 MHz, CDCl$_3$) δ 29.6; IR (neat, v/cm$^{-1}$) 2930, 2858, 1730, 1639, 1494, 1359, 1143, 964, 855, 795; HRMS (ESI+) Calcd for $C_{27}H_{44}BNNaO_5$([M+Na]+) 496.3205, Found 496.3186.

(9) N,N-Dihexyl-4-(4,4,5,5-tetramethyl-1,3,2-dioxaborolan-2-yl)-[1,1'-biphenyl]-2-carboxamide

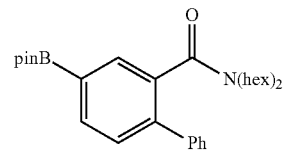

26% yield; colorless oil; $^1$HNMR (400 MHz, CDCl$_3$) δ 0.79(t, J=7.2 Hz, 3H), 0.88 (t, J=7.0 Hz, 3H), 0.92-1.01(m, 4H), 1.05-1.28 (m, 10H), 1.34 (s, 12H), 1.62-1.66 (m, 2H), 2.48-2.54 (m, 1H), 2.80-2.98 (m, 2H), 3.54-3.61 (m, 1H), 7.30-7.41 (m, 4H), 7.48-7.50 (m, 2H), 7.82 (s, 1H), 7.85 (dd, J=7.9, 1.1 Hz, 1H); $^{13}$C NMR (100 MHz, CDCl$_3$) δ 14.1, 14.2, 22.5, 22.7, 24.8, 25.1, 26.2, 26.9, 27.9, 31.3, 31.8, 44.4, 48.3, 84.0, 127.8, 128.4, 128.7, 128.9, 134.1, 135.2, 136.0, 140.0, 141.0, 171.1; $^{11}$B NMR (130 MHz, CDCl$_3$) δ 31.8; IR (neat, v/cm$^{-1}$) 2928, 2857, 1629, 1466, 1387, 1318, 1144, 965, 700, 611; HRMS (ESI$^+$) Calcd for C$_{31}$H$_{46}$BNNaO$_3$ ([M+Na]$^+$) 514.3463, Found 514.3452.

(10) 2-Methyl-6-(4,4,5,5-tetramethyl-1,3,2-dioxaborolan-2-yl)-isoindolin-1-one, and 2-methyl-5-(4,4,5,5-tetramethyl-1,3,2-dioxaborolan-2-yl)-isoindolin-1-one

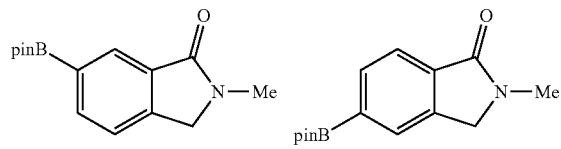

39% yield [meta/para=3.3]; pale yellow solid; $^{11}$B NMR (130 MHz, CDCl$_3$) δ 30.8; IR (neat, v/cm$^{-1}$) 2978, 2932, 1680, 1397, 1355, 1337, 1309, 1258, 1202, 1143, 1115, 967, 863, 849, 714, 655; HRMS (ESI$^+$) Calcd for C$_{15}$H$_{20}$BNNaO$_3$([M+Na]$^+$) 296.1434, Found 296.1438.

2-Methyl-6-(4,4,5,5-tetramethyl-1,3,2-dioxaborolan-2-yl)-isoindolin-1-one: $^1$H NMR (400 MHz, CDCl$_3$) δ 1.35 (s, 12H), 3.18 (s, 3H), 4.36 (s, 2H), 7.41 (d, J=7.6 Hz, 1H), 7.93 (d, J=7.6 Hz, 1H), 8.29 (s, 1H); $^{13}$C NMR (125 MHz, CDCl$_3$) δ 24.8, 29.4, 52.1, 84.0, 121.9, 130.1, 132.3, 137.3, 143.8, 168.5.

2-Methyl-5-(4,4,5,5-tetramethyl-1,3,2-dioxaborolan-2-yl)-isoindolin-1-one: $^1$H NMR (400 MHz, CDCl$_3$) δ 1.35 (s, 12H), 3.19 (s, 3H), 4.35 (s, 2H), 7.81 (d, J=7.6 Hz, 1H), 7.86 (s, 1H), 7.89 (d, J=7.6 Hz, 1H); $^{13}$C NMR (125 MHz, CDCl$_3$) δ 24.9, 29.5, 51.9, 84.2, 122.7, 128.7, 134.3, 135.2, 140.1, 168.6.

(11) N,N-Dimethyl-3-(4,4,5,5-tetramethyl-1,3,2-dioxaborolan-2-yl)benzamide and N,N-dimethyl-4-(4,4,5,5-tetramethyl-1,3,2-dioxaborolan-2-yl)benzamide

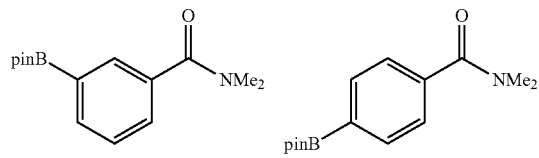

41% yield [meta/para=13]; white solid; $^{11}$B NMR (130 MHz, CDCl$_3$) δ 30.6; IR (neat, v/cm$^{-1}$) 2978, 1634, 1482, 1356, 1267, 1213, 965, 812, 709, 671; HRMS (ESI$^+$) Calcd for C$_{15}$H$_{22}$BNNaO$_3$ ([M+Na]$^+$) 298.1585, Found 298.1585.

N,N-Dimethyl-3-(4,4,5,5-tetramethyl-1,3,2-dioxaborolan-2-yl)benzamide: $^1$H NMR (500 MHz, CDCl$_3$) δ 1.34 (s, 12H), 2.96 (s, 3H), 3.10 (s, 3H), 7.40 (dd, J=8.0, 8.0 Hz, 1H), 7.49 (ddd, J=8.1, 1.1, 1.1 Hz, 1H), 7.82-7.84 (m, 2H); $^{13}$C NMR (100 MHz, CDCl$_3$) δ 25.0, 35.4, 39.7, 84.1, 127.9, 129.8, 133.2, 135.8, 135.9, 171.8.

N,N-Dimethyl-4-(4,4,5,5-tetramethyl-1,3,2-dioxaborolan-2-yl)benzamide: $^1$H NMR (400 MHz, CDCl$_3$) δ 1.35 (s, 12H), 3.19 (s, 3H), 4.35 (s, 2H), 7.81 (d, J=7.6 Hz, 1H), 7.86 (s, 1H), 7.89 (d, J=7.6 Hz, 1H); $^{13}$C NMR (125 MHz, CDCl$_3$) δ 24.9, 29.5, 51.9, 84.2, 122.7, 128.7, 134.3, 135.2, 140.1, 168.6.

N,N-Dimethyl-3,5-bis(4,4,5,5-tetramethyl-1,3,2-dioxaborolan-2-yl)benzamide

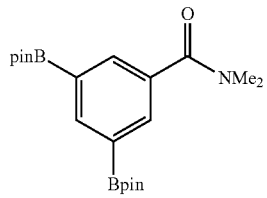

11% yield; white solid; $^1$H NMR (400 MHz, CDCl$_3$) δ 1.33 (s, 24H), 2.95 (s, 3H), 3.09 (s, 3H), 7.93 (d, J=1.3 Hz, 2H), 8.28 (t, J=1.3 Hz, 1H); $^{13}$C NMR (100 MHz, CDCl$_3$) δ 25.0, 35.3, 39.8, 84.1, 135.5, 135.9, 142.1, 171.9; $^{11}$B NMR (130 MHz, CDCl$_3$) δ30.6; IR (neat, v/cm$^{-1}$) 2978, 1636, 1594, 1380, 1330, 1213, 1142, 889, 755, 689; HRMS (ESI$^+$) Calcd for C$_{21}$H$_{33}$B$_2$NNaO$_5$([M+Na]$^+$) 424.2437, Found 424.2455.

(12) 1-Piperidinyl(3-(4,4,5,5-tetramethyl-1,3,2-dioxaborolan-2-yl)phenyl)methanone

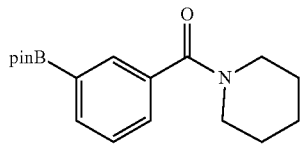

50% yield; white solid; $^1$H NMR (400 MHz, CDCl$_3$) δ 1.34 (s, 12H), 1.48-1.51 (m, 2H), 1.63-1.70 (m, 4H), 3.29-3.37 (m, 2H), 3.67-3.73 (m, 2H), 7.38 (dd, J=7.6, 6.7 Hz, 1H), 7.46 (d, J=7.6 Hz, 1H), 7.81-7.82 (m, 2H); $^{13}$C NMR (100 MHz, CDCl$_3$) δ 24.7, 25.0, 25.7, 26.6, 43.1, 48.9, 84.1, 127.8, 129.5, 133.1, 135.7, 136.1, 170.4; $^{11}$B NMR (130 MHz, CDCl$_3$) δ 30.8; IR (neat, v/cm$^{-1}$) 2938, 1714, 1626, 1358, 1271, 1143, 1094, 964, 859, 754, 666; HRMS (ESI$^+$) Calcd for C$_{18}$H$_{26}$BNNaO$_3$([M+Na]$^+$) 338.1898, Found 338.1897.

1-Piperidinyl(3,5-bis(4,4,5,5-tetramethyl-1,3,2-dioxaborolan-2yl)phenyl)methanone:

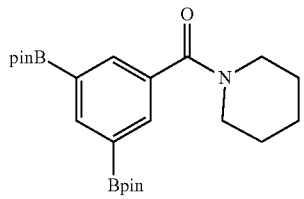

11% yield; white solid; $^1$H NMR (400 MHz, CDCl$_3$) δ 1.37 (s, 24H), 1.49-1.65 (m, 6H), 3.32-3.33 (m, 2H), 3.64-3.70 (m, 2H), 7.89 (s, 2H), 8.27 (s, 1H); $^{13}$C NMR (100 MHz, CDCl$_3$) δ 24.7, 25.0, 25.7, 26.6, 43.1, 48.9, 84.1, 135.6, 135.8, 142.1, 170.5; $^{11}$B NMR (130 MHz, CDCl$_3$) δ

30.8; IR (neat, v/cm⁻¹) 2979, 1624, 1329, 1267, 1142, 966, 889, 755, 716, 666; HRMS (ESI⁺) Calcd for $C_{24}H_{37}B_2NNaO_5$ ([M+Na]⁺) 464.2750, Found 464.2728.

(13) (2-Bromo-5-(4,4,5,5-tetramethyl-1,3,2-dioxaborolan-2-yl)phenyl)-4-morpholinylmethanone and (2-bromo-4-(4,4,5,5-tetramethyl-1,3,2-dioxaborolan-2-yl)phenyl)-4-morpholinylmethanone

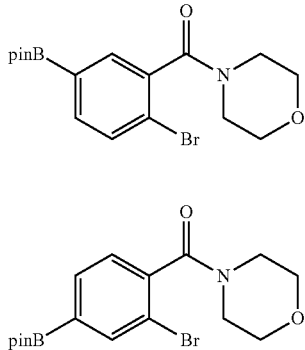

88% yield [meta/para=3.2]; pale yellow solid; ¹¹B NMR (130 MHz, CDCl₃) δ30.8; IR (KBr, v/cm⁻¹) 2977, 2927, 2857, 1645, 1592, 1434, 1386, 1356, 1280, 1248, 1143, 1114, 1094, 1016, 848, 689; HRMS (ESI⁺) Calcd for $C_{17}H_{23}BBrNNaO_4$ ([M+Na]⁺) 418.0801, Found 418.0791.

(2-Bromo-5-(4,4,5,5-tetramethyl-1,3,2-dioxaborolan-2-yl)phenyl)-4-morpholinylmethanone: ¹H NMR (500 MHz, CDCl₃) δ 1.30 (s, 12H), 3.10-3.29 (m, 2H), 3.50-3.61 (m, 1H), 3.64-3.80 (m, 4H), 3.80-3.89 (m, 1H), 7.55 (d, J=8.0 Hz, 1H), 7.62 (dd, J=8.0, 1.8 Hz, 1H), 7.65 (d, J=1.8 Hz, 1H); ¹³C NMR (125 MHz, CDCl₃) δ 24.9, 41.8, 47.0, 66.5, 66.6, 84.2, 122.4, 132.0, 133.8, 136.4, 138.7, 167.7.

(2-Bromo-4-(4,4,5,5-tetramethyl-1,3,2-dioxaborolan-2-yl)phenyl)-4-morpholinylmethanone: ¹H NMR (500 MHz, CDCl₃) δ 1.28 (s, 12H), 3.10-3.29 (m, 2H), 3.50-3.61 (m, 1H), 3.64-3.80 (m, 4H), 3.80-3.89 (m, 1H), 7.22 (d, J=7.5 Hz, 1H), 7.74 (d, J=7.5 Hz, 1H), 7.97 (s, 1H); ¹³C NMR (125 MHz, CDCl₃) δ24.5, 41.8, 47.0, 66.5, 66.6, 84.3, 118.8, 127.0, 133.8, 136.9, 139.8, 167.5.

(14) Azepane-1-yl(3-(4,4,5,5-tetramethyl-1,3,2-dioxaborolan-2-yl)phenyl)methanone

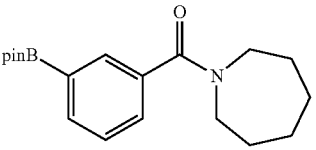

36% yield; white solid; ¹H NMR (400 MHz, CDCl₃) δ 1.34 (s, 12H), 1.59-1.64 (m, 6H), 1.81-1.85 (m, 2H), 3.36 (t, J=5.4 Hz, 2H), 3.67 (t, J=5.8 Hz, 2H), 7.38 (dd, J=7.9, 7.6 Hz, 1H), 7.46 (d, J=7.9 Hz, 1H), 7.80-7.82 (m, 2H); ¹³C NMR (100 MHz, CDCl₃) δ 25.0, 26.6, 27.4, 28.0, 29.6, 46.3, 49.9, 84.1, 127.8, 129.2, 132.8, 135.4, 136.9, 171.7; ¹¹B NMR (130 MHz, CDCl₃) δ 30.6; IR (neat, v/cm⁻¹) 2977, 2928, 1631, 1409, 1356, 1319, 1216, 1099, 859, 708; HRMS (ESI⁺) Calcd for $C_{19}H_{28}BNNaO_3$ ([M+Na]⁺) 352.2054, Found 352.2049.

Azepane-1-yl(3,5-bis(4,4,5,5-tetramethyl-1,3,2-dioxaborolan-2-yl)phenyl)methanone

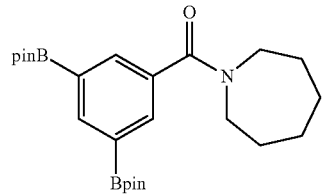

12%; yield; white solid; ¹H NMR (400 MHz, CDCl₃) δ 1.33 (s, 24H), 1.58-1.59 (m, 6H), 1.80-1.86 (m, 2H), 3.36 (t, J=5.4 Hz, 2H), 3.65 (t, J=5.4 Hz, 2H), 7.90 (s, 2H), 8.27 (s, 1H); ¹³C NMR (100 MHz, CDCl₃) δ 25.0, 26.7, 27.5, 28.1, 29.6, 46.1, 50.0, 84.1, 135.5, 136.3, 141.8, 171.8; ¹¹B NMR (130 MHz, CDCl₃) δ 31.3; IR (neat, v/cm⁻¹) 2930, 2927, 1628, 1429, 1389, 1270, 1142, 889, 754, 689; HRMS (ESI⁺) Calcd for $C_{25}H_{39}B_2NNaO_5$ ([M+Na]⁺) 478.2907, Found 478.2926.

(15) N,N-Dihexyl-2-(trifluoromethyl)-5-(4,4,6-trimethyl-1,3,2-dioxaborolan-2-yl)benzamide and N,N-dihexyl-2-(trifluoromethyl)-4-(4,4,6-trimethyl-1,3,2-dioxaborolan-2-yl)benzamide

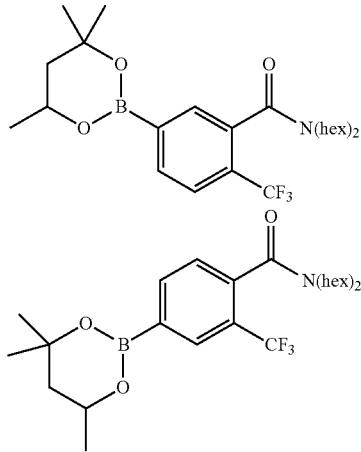

62% yield [meta/para=5.3]; colorless oil; ¹¹B NMR (130 MHz, CDCl₃) δ 26.2; IR (neat, v/cm⁻¹) 2931, 1644, 1502, 1408, 1306, 1170, 1039, 844, 767, 687; HRMS (ESI⁺) Calcd for $C_{26}H_{41}BF_3NNaO_3$([M+Na]⁺) 506.3024, Found 506.3013.

N,N-Dihexyl-2-(trifluoromethyl)-5-(4,4,6-trimethyl-1,3,2-dioxaborolan-2-yl)benzamide: ¹H NMR (500 MHz, CDCl₃) δ 0.81 (t, J=7.2 Hz, 3H), 0.89-0.92 (m, 3H), 1.08-1.09 (m, 4H), 1.17-1.21 (m, 2H), 1.33-1.47 (m, 18H), 1.61-1.64 (m, 2H), 1.86-1.91 (m, 1H), 2.95-3.00 (m, 2H), 3.12-3.19 (m, 1H), 3.77-3.84 (m, 1H), 4.13-4.37 (m, 1H), 7.60 (d, J=7.6 Hz, 1H), 7.75 (s, 1H), 7.87 (d, J=7.6 Hz, 1H); ¹³C NMR (100 MHz, CDCl₃) δ 14.0, 14.1, 22.5, 22.7, 23.1, 26.2, 26.4, 26.9, 28.0, 28.2, 31.2, 31.4, 31.7, 44.4, 46.0, 48.7, 65.4, 71.6, 124.0 (q, J=274 Hz), 125.2 (q, J=3.6 Hz), 126.4, 127.6 (q, J=32.3 Hz), 132.9, 133.9, 169.2; ¹⁹F NMR (368 MHz, CDCl₃) δ −61.9.

N,N-Dihexyl-2-(trifluoromethyl)-4-(4,4,6-trimethyl-1,3, 2-dioxaborolan-2-yl)benzamide: ¹H NMR (500 M Hz, CDCl$_3$) δ 0.81 (t, J=7.2 Hz, 3H), 0.89-0.92 (m, 3H), 1.08-1.09 (m, 4H), 1.17-1.21 (m, 2H), 1.33-1.47 (m, 18H), 1.61-1.64 (m, 2H), 1.86-1.91 (m, 1H), 2.95-3.00 (m, 2H), 3.12-3.19 (m, 1H), 3.77-3.84 (m, 1H), 4.13-4.37 (m, 1H), 7.26 (d, J=6.7 Hz, 1H), 7.96 (d, J=6.7 Hz, 1H), 8.08 (s, 1H); $^{13}$C NMR (100 MHz, CDCl$_3$) δ 14.0, 14.1, 22.4, 22.7, 23.1, 26.2, 26.4, 26.9, 28.0, 28.2, 31.2, 31.3, 31.7, 44.4, 46.0, 48.7, 65.4, 71.6, 124.3 (q, J=296 Hz), 125.7, 127.6 (q, J=32.3 Hz), 131.8 (q, J=4.8 Hz), 134.6, 169.2; $^{19}$F NMR (368 MHz, CDCl$_3$) δ -61.5.

(16) 3-Fluoro-N,N-dihexyl-5-(4,4,5,5-tetramethyl-1,3,2-dioxaborolan-2-yl)benzamide and 3-fluoro-N,N-dihexyl-4-(4,4,5,5-tetramethyl-1,3,2-dioxaborolan-2-yl)benzamide

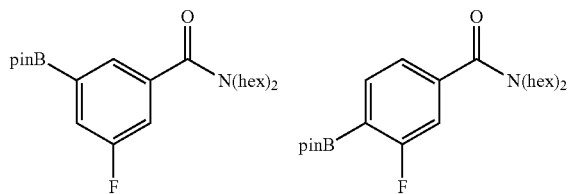

99% yield [meta/para=7.7]; colorless oil; $^{11}$H NMR (130 MHz, CDCl$_3$) δ 30.0; IR (neat, v/cm$^{-1}$) 2929, 1633, 1368, 1143, 1099, 968, 923, 854, 756, 676; HRMS (ESI$^+$) Calcd for C$_{25}$H$_{41}$FNNaO$_3$ ([M+Na]$^+$) 456.3056, Found 456.3035.

3-Fluoro-N,N-dihexyl-5-(4,4,5,5-tetramethyl-1,3,2-dioxaborolan-2-yl)benzamide: $^1$H NMR (400 MHz, CDCl$_3$) δ 0.82 (t, J=6.7 Hz, 3H), 0.89-0.91 (m, 3H), 1.12-1.17 (m, 4H), 1.21-1.49 (m, 22H), 1.61-1.62 (m, 2H), 3.14 (t, J=7.2 Hz, 2H), 3.44 (t, J=7.2 Hz, 2H), 7.13 (d, J=8.8 Hz, 1H), 7.48 (d, J=8.8 Hz, 1H), 7.55 (s, 1H); $^{13}$C NMR (100 MHz, CDCl$_3$) δ 14.0, 14.1, 22.5, 22.7, 24.9, 26.2, 26.8, 27.5, 28.7, 31.3, 31.7, 45.0, 49.1, 84.3, 116.5 (d, J=22.6 Hz), 121.6 (d, J=19.7 Hz), 128.2 (d, J=2.8Hz), 138.9 (d, J=6.6 Hz), 162.2 (d, J=248 Hz), 170.1; $^{19}$F NMR (368 MHz, CDCl$_3$) δ -115.3 (s, 1F).

3-Fluoro-N,N-dihexyl-4-(4,4,5,5-tetramethyl-1,3,2-dioxaborolan-2-yl)benzamide: $^1$H NMR (400 MHz, CDCl$_3$) δ 0.82 (t, J=6.7 Hz, 3H), 0.89-0.91 (m, 3H), 1.12-1.18 (m, 4H), 1.21-1.49 (m, 22H), 1.61-1.62 (m, 2H), 3.14 (t, J=7.2 Hz, 2H), 3.44 (t, J=7.2 Hz, 2H), 7.01 (d, J=9.0 Hz, 1H), 7.11 (d, J=9.0 Hz, 1H), 7.73-7.77 (m, 1H); $^{13}$C NMR (100 MHz, CDCl$_3$) δ 14.0, 14.1, 22.5, 22.7, 24.9, 26.2, 26.8, 27.5, 28.7, 31.3, 31.7, 44.8, 49.0, 84.2, 113.6 (d, J=26.3 Hz), 132.0 (br), 137.1 (d, J=8.4 Hz), 142.4 (d, J=7.5 Hz), 165.4 (d, J=253 Hz), 169.9; $^{19}$F NMR (368 MHz, CDCl$_3$) δ -103.7 (s, 1F).

(17) 3-Bromo-N,N-dihexyl-5-(4,4,5,5-tetramethyl-1,3,2-dioxaborolan-2-yl)benzamide

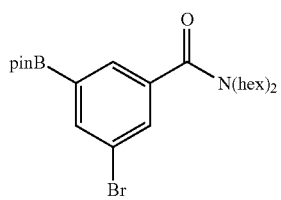

86% yield; pale yellow oil; $^1$H NMR (400 MHz, CDCl$_3$) δ 0.83 (t, J=7.2 Hz, 3H), 0.89-0.91 (m, 3H), 1.12-1.17 (m, 4H), 1.21-1.33 (m, 20H), 1.49-1.63 (m, 4H), 3.13 (t, J=7.6 Hz, 2H), 3.43 (t, J=7.6 Hz, 2H), 7.56 (s, 1H), 7.69 (s, 1H), 7.93 (s, 1H); $^{13}$C NMR (100 MHz, CDCl$_3$) δ14.0, 14.1, 22.5, 22.7, 24.9, 26.2, 26.8, 27.5, 28.7, 31.3, 31.7, 45.0, 49.1, 84.4, 122.4, 131.0, 132.1, 138.0, 138.8, 169.9; $^{11}$B NMR (130 MHz, CDCl$_3$) δ 30.7; IR (neat, v/cm$^{-1}$) 2929, 2857, 1635, 1435, 1348, 1143, 965, 964, 885, 704; HRMS (ESI$^+$) Calcd for C$_{25}$H$_{41}$BBrNNaO$_3$ ([M+Na]$^+$) 516.2255, Found 516.2255.

(18) N,N-Dihexyl-5-(4,4,5,5-tetramethyl-1,3,2-dioxaborolan-2-yl)-[1,1'-biphenyl]-3-carboxamide

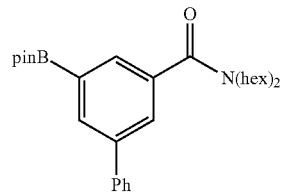

81% yield; pale yellow oil; $^1$H NMR (400 MHz, CDCl$_3$) δ 0.79 (t, J=7.2 Hz, 3H), 0.90-0.92 (m, 3H), 1.11-1.19 (m, 6H), 1.23-1.35 (m, 18H), 1.51-1.53 (m, 2H), 1.63-1.66 (m, 2H), 3.20 (t, J=7.6 Hz, 2H), 3.48 (t, J=8.1 Hz, 2H), 7.34 (t, J=7.4 Hz, 1H), 7.43 (dd, J=8.1, 7.4 Hz, 2H), 7.62 (d, J=8.1 Hz, 2H), 7.66 (s, 1H), 7.76 (s, 1H), 8.05 (s, 1H); $^{13}$C NMR (100 MHz, CDCl$_3$) δ 14.1, 14.2, 22.5, 22.8, 25.0, 26.3, 27.0, 27.7, 28.9, 31.4, 31.8, 45.0, 49.3, 84.2, 127.3, 127.6, 128.0, 128.8, 131.6, 134.1, 137.5, 140.6, 140.8, 171.6; $^{11}$B NMR (130 MHz, CDCl$_3$) δ 32.5; IR (neat, v/cm$^{-1}$) 2929, 2857, 1634, 1411, 1321, 1144, 966, 894, 756, 698; HRMS (ESI$^+$) Calcd for C$_{31}$H$_{46}$BNNaO$_3$ ([M+Na]$^+$) 514.3463, Found 514.3456.

(19) 3-Cyano-N,N-dihexyl-5-(4,4,5,5-tetramethyl-1,3,2-dioxaborolan-2-yl)benzamide

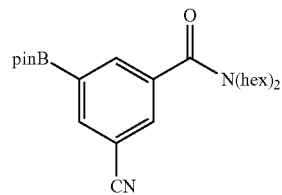

87% yield; pale yellow oil; $^1$H NMR (400 MHz, CDCl$_3$) δ 0.82 (t, J=7.2 Hz, 3H), 0.88-0.90 (m, 3H), 1.11-1.42 (m, 24H), 1.48-1.52 (m, 2H), 1.65-1.69 (m, 2H), 3.11 (t, J=7.6 Hz, 2H), 3.43 (t, J=7.6 Hz, 2H), 7.69 (dd, J=1.6, 1.6 Hz, 1H), 7.97 (dd, J=1.6, 1.4 Hz, 1H), 8.08 (dd, J=1.6, 1.4 Hz, 1H); $^{13}$C NMR (100 MHz, CDCl$_3$) δ14.0, 14.1, 22.4, 22.6, 24.9, 26.2, 26.8, 27.5, 28.7, 31.2, 31.6, 45.1, 49.2, 84.8, 112.4, 118.2, 132.3, 136.6, 137.9, 138.7, 169.2; $^{11}$B NMR (130 MHz, CDCl$_3$) δ 30.3; IR (neat, v/cm$^{-1}$) 2930, 2857, 2231, 1637, 1371, 1265, 1143, 966, 850, 704; HRMS (ESI$^+$) Calcd for C$_{26}$H$_{41}$BN$_2$NaO$_3$ ([M+Na]$^+$) 463.3102, Found 463.3124.

(20) 2,3-Dichloro-N,N-dihexyl-5-(4,4,5,5-tetramethyl-1,3,2-dioxaborolan-2-yl)benzamide

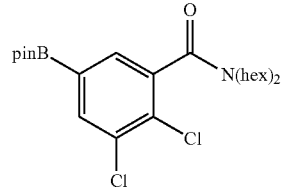

94% yield; pale yellow oil; $^1$H NMR (500 MHz, CDCl$_3$) δ 0.81 (t, J=7.5 Hz, 3H), 0.91 (t, J=6.7 Hz, 3H), 1.08-1.11 (m, 4H), 1.18-1.21 (m, 2H), 1.32-1.50 (m, 20H), 1.65-1.70 (m, 2H), 2.98-3.02 (m, 1H), 3.05-3.09 (m, 1H), 3.26-3.31 (m, 1H), 3.64-3.70 (m, 1H), 7.56 (d, J=1.2 Hz, 1H), 7.85 (d, J=1.2 Hz, 1H); $^{13}$C NMR (100 MHz, CDCl$_3$) δ 14.0, 14.1, 22.4, 22.7, 24.9 (br), 26.2, 26.8, 27.3, 28.3, 31.2, 31.7, 44.7, 48.5, 84.6, 131.6, 131.9, 133.1, 136.3, 138.4, 167.3; $^{11}$B NMR (130 MHz, CDCl$_3$) δ30.4; IR (neat, ν/cm$^{-1}$) 2930, 2858, 1644, 1467, 1350, 1268, 1142, 965, 894, 755; HRMS (ESI$^+$) Calcd for C$_{25}$H$_{40}$BCl$_2$NNaO$_3$ ([M+Na]$^+$) 506.2371, Found 506.2394.

(21) 2-Fluoro-N,N-dihexyl-5-(4,4,5,5-tetramethyl-1,3,2-dioxaborolan-2-yl)-3-(trifluoromethyl)benzamide

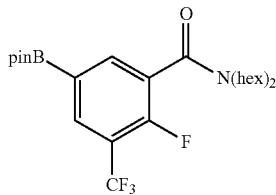

89% yield; pale yellow oil; $^1$H NMR (400 MHz, CDCl$_3$) δ 0.80 (t, J=7.2 Hz, 3H), 0.90 (t, J=6.7 Hz, 3H), 1.08-1.11 (m, 4H), 1.17-1.22 (m, 2H), 1.33-1.49 (m, 20H), 1.65-1.67 (m, 2H), 3.14 (t, J=7.6 Hz, 2H), 3.40-3.64 (m, 2H), 7.94 (d, J=6.3 Hz, 1H), 8.05 (d, J=7.2 Hz, 1H); $^{13}$C NMR (100 MHz, CDCl$_3$) δ 13.9, 14.1, 22.4, 22.6, 24.9, 26.1, 26.7, 27.4, 28.4, 31.2, 31.7, 44.9, 48.8, 84.7, 118.4 (qd, J=33.6, 12.0 Hz), 122.5 (q, J=272 Hz), 126.6 (d, J=18.0 Hz), 134.1 (d, J=3.6 Hz), 139.2 (d, J=4.8 Hz), 157.3 (d, J=260 Hz), 165.0; $^{19}$F NMR (368 MHz, CDCl$_3$) δ −115.4 (s, 1F), −63.1 (s, 3F); $^{11}$B NMR (130 MHz, CDCl$_3$) δ 30.1; IR (neat, ν/cm$^{-1}$) 2931, 1644, 1468, 1385, 1302, 1239, 1197, 914, 756, 672; HRMS (ESI$^+$) Calcd for C$_{26}$H$_{40}$BF$_4$NNaO$_3$ ([M+Na]$^+$) 524.2930, Found 524.2939.

(22) N,N-Dihexyl-2-(5-(4,4,5,5-tetramethyl-1,3,2-dioxaborolan-2-yl)thiophene)carboxamide

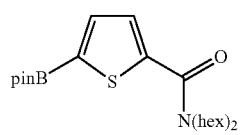

51% yield; pale yellow oil; $^1$H NMR (500 MHz, CDCl$_3$) δ 0.80-0.92 (m, 6H), 1.16-1.38 (m, 12H), 1.33 (s, 12H), 1.53-1.70 (m, 4H), 3.38-3.44 (m, 4H), 7.30 (d, J=3.6 Hz, 1H), 7.50 (d, J=3.6 Hz, 1H); $^{13}$C NMR (125 MHz, CDCl$_3$) δ 13.9 (2C), 22.5, 24.7 (2C), 26.4 (br, 2C), 27.5 (br), 28.8 (br), 31.4 (2C), 46.1 (br), 49.3 (br), 84.3, 129.1, 136.3, 144.2, 164.3; $^{11}$B NMR (130 MHz, CDCl$_3$) δ 29.0; IR (neat, ν/cm$^{-1}$) 2956, 2929, 2862, 1625, 1525, 1463, 1419, 1372, 1350, 1287, 1270, 1210, 1143, 1063, 1021, 997, 857, 853, 820, 739, 687, 667; HRMS (ESI$^+$) Calcd for C$_{23}$H$_{40}$BNNaO$_3$S ([M+Na]$^+$) 444.2720, Found 444.2731.

N,N-Dihexyl-2-(3,5-bis(4,4,5,5-tetramethyl-1,3,2-dioxaborolan-2-yl)thiophene)carboxamide

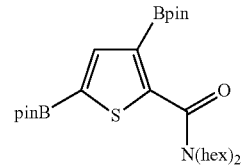

14% yield; pale brown oil; $^1$H NMR (500 MHz, CDCl$_3$) δ 0.75-0.96 (m, 6H), 1.03-1.53 (m, 40H), 3.05-3.22 (m, 2H), 3.35-3.55 (m, 2H), 7.83 (s, 1H); $^{13}$C NMR (125 MHz, CDCl$_3$) δ 13.97, 14.03, 22.4, 22.6, 24.7, 24.8, 26.2, 26.9, 27.0, 28.3, 31.3, 31.7, 45.2, 49.0, 83.6, 84.2, 143.1, 153.2, 165.5; $^{11}$B NMR (130 MHz, CDCl$_3$) δ 28.6; IR (neat, ν/cm$^{-1}$) 3424, 2929, 2859, 1633, 1536, 1455, 1371, 1321, 1268, 1213, 1139, 1111, 1028, 1002, 967, 911, 882, 851, 829, 727, 688, 666; HRMS (ESI$^+$) Calcd for C$_{29}$H$_{51}$B$_2$NNaO$_5$S ([M+Na]$^+$) 570.3572, Found 570.3551.

(23) N,N-Dihexyl-5-(4,4,5,5-tetramethyl-1,3,2-dioxaborolan-2-yl)-1H-pyrrole-2-carboxamide

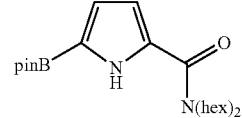

79% yield; colorless oil; $^1$H NMR (400 MHz, CDCl$_3$) δ 0.81-0.93 (m, 6H), 1.23-1.36 (m, 24H), 1.53-1.78 (m, 4H), 3.25-3.70 (m, 4H), 6.43-6.70 (m, 1H), 6.74-6.78 (m, 1H), 9.85 (brs, 1H); $^{13}$C NMR (125 MHz, CDCl$_3$) δ 14.0 (2C), 22.5, 24.7 (2C), 26.6 (2C), 27.6 (br), 28.8 (br), 31.5 (2C), 47.2 (br), 48.5 (br), 83.8, 111.6, 120.2, 129.2, 161.5; $^{11}$B NMR (130 MHz, CDCl$_3$) δ 28.3; IR (neat, ν/cm$^{-1}$) 3441, 3256, 2929, 2858, 1610, 1553, 1467, 1424, 1345, 1300, 1265, 1219, 1144, 973, 855, 790, 759, 704; HRMS (BSI$^+$) Calcd for C$_{23}$H$_{41}$BN$_2$NaO$_3$ ([M+Na]$^+$) 427.3108, Found 427.3114.

(24) N,N-Dihexyl-(1-methyl-5-(4,4,5,5-tetramethyl-1,3,2-dioxaborolan-2-yl)-1H-pyrrole)-2-carboxamide and N,N-dihexyl-(1-methyl-4-(4,4,5,5-tetramethyl-1,3,2-dioxaborolan-2-yl)-1H-pyrrole)-2⁻carboxamide 74% yield [5−/4−=6.7]; pale yellow oil; $^{11}$B NMR (130 MHz, CDCl$_3$) δ 28.3; IR (neat, ν/cm$^{-1}$) 2929, 2858, 1628, 1531, 1467, 1416, 1373, 1302, 1265, 1145, 1108, 1091, 965, 858, 754, 692; HRMS (ESI$^+$) Calcd for C$_{24}$H$_{43}$BN$_2$NaO$_3$ ([M+Na]$^+$) 441.3264, Found 441.3255.

N,N-Dihexyl-(1-methyl-5-(4,4,5,5-tetramethyl-1,3,2-dioxaborolan-2-yl)-1H-pyrrole)-2-carboxamide: $^1$H NMR (500 MHz, CDCl$_3$) δ 0.78-0.94 (m, 6H), 1.10-1.40 (m, 24H), 1.42-1.75 (m, 4H), 3.26-3.54 (m, 4H), 3.82 (s, 3H), 6.20 (d, J=4.0 Hz, 1H), 6.70 (d, J=4.0 Hz, 1H); $^{13}$C NMR (125 MHz, CDCl$_3$) δ 13.9 (2C), 22.5 (2C), 24.7, 26.4 (br, 2C), 27.5 (br), 28.6 (br), 31.4 (2C), 34.6, 44.6 (br), 48.9 (br), 83.2, 109.7, 120.2, 132.5, 164.5.

N,N-Dihexyl-(1-methyl-4-(4,4,5,5-tetramethyl-1,3,2-dioxaborolan-2-yl)-1H-pyrrole)-2-carboxamide: $^1$H NMR (500 MHz, CDCl$_3$) δ 0.78-0.94 (m, 6H), 1.10-1.40 (m, 24H), 1.42-1.75 (m, 4H), 3.26-3.54 (m, 4H), 3.71 (s, 3H), 6.56-6.60 (m, 1H), 7.04-7.11 (m, 1H); $^{13}$C NMR (125 MHz, CDCl$_3$) δ13.9 (2C), 22.5 (2C), 24.7, 26.4 (2C), 27.5 (br), 28.6 (br), 31.4 (2C), 35.6, 44.6 (br), 48.9 (br), 82.9, 117.0, 127.6, 134.0, 164.0.

(25) N,N-Dihexyl-(7-(4,4,5,5-tetramethyl-1,3,2-dioxaborolan-2-yl)-1H-indole)-2-carboxamide

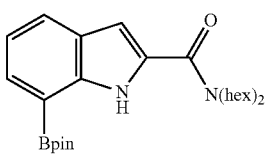

71% yield; pale yellow oil; $^1$H NMR (500 MHz, CDCl$_3$) δ 0.87-0.96 (m, 6H), 1.30-1.41 (m, 12H), 1.39 (s, 12H), 1.60-1.85 (m, 4H), 3.30-3.90 (m, 4H), 6.75 (d, J=2.3 Hz, 1H), 7.15 (t, J=8.0 Hz, 1H), 7.75 (d, J=8.0 Hz, 1H), 7.78 (d, J=8.0 Hz, 1H), 9.94 (brs, 1H); $^{13}$C NMR (125 MHz, CDCl$_3$) δ 14.0 (2C), 22.5 (2C), 24.9, 26.6 (br, 2C), 27.6 (br), 28.8 (br), 31.5 (2C), 47.4 (br), 49.0 (br), 83.9, 103.9, 119.9, 125.3, 126.9, 129.9, 131.7, 140.0, 162.5; $^{11}$B NMR (130 MHz, CDCl$_3$) δ 31.2; IR (neat, v/cm$^{-1}$) 3438, 3056, 2927, 2857, 1615, 1595, 1529, 1463, 1443, 1369, 1288, 1200, 1146, 1130, 1110, 1045, 979, 849, 813, 748, 734, 678; HRMS (ESI$^+$) Calcd for C$_{27}$H$_{43}$BN$_2$NaO$_3$ ([M+Na]$^+$) 477.3264 Found 477.3264.

(26) N,N-Dimethyl-4-(4,4,5,5-tetramethyl-1,3,2-dioxaborolan-2-yl)picolinamide and N,N-Dimethyl-5-(4,4,5,5-tetramethyl-1,3,2-dioxaborolan-2-yl)picolinamide

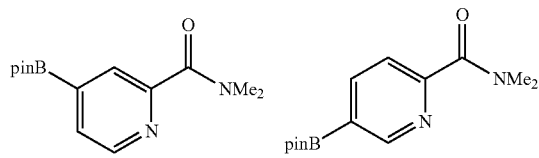

43% yield [4-/5-=3.6]; white solid; $^{13}$C NMR (100 MHz, CDCl$_3$) δ (4- and 5-position isomers) 25.0 (4- and 5-position isomers), 35.71, 35.76, 39.0, 39.1, 84.6, 84.8, 122.7, 128.5, 129.3, 143.4, 147.9, 154.07, 154.13, 156.5, 169.4 (4- and 5-position isomers); $^{11}$B NMR (130 MHz, CDCl$_3$) δ 30.6; IR (neat, v/cm$^{-1}$) 2979, 1640, 1473, 1358, 1263, 1105, 965, 857, 752, 672; HRMS (ESI$^+$) Calcd for C$_{14}$H$_{21}$BN$_2$N$_2$NaO$_3$ ([M+Na]$^+$) 299.1537, Found 299.1534.

N,N-Dimethyl-4-(4,4,5,5-tetramethyl-1,3,2-dioxaborolan-2-yl)picolinamide: $^1$H NMR (500 MHz, CDCl$_3$) δ 1.34 (s, 12H), 3.04 (s, 3H), 3.13 (s, 3H), 7.65 (d, J=5.8 Hz, 1H), 7.96 (s, 1H), 8.60 (d, J=5.8 Hz, 1H).

N,N-Dimethyl-5-(4,4,5,5-tetramethyl-1,3,2-dioxaborolan-2-yl)picolinamide: $^1$H NMR (500 MHz, CDCl$_3$) δ 1.36 (s, 12H), 3.04 (s, 3H), 3.13 (s, 3H), 7.58 (d, J=7.8 Hz, 1H), 8.15 (d, J=7.8 Hz, 1H), 8.91 (s, 1H).

As can be seen from the above-described results, the borylation of aromatic compounds by the catalyst of the present invention results in the meta-selective borylation.
[0182]

(27) Table 1 shows the meta-para selectivity (m/p) in the case where the borylation reaction was performed in the same manner as Example 9(1) by using the ligands described in Examples 2 to 6.

TABLE 1

| R$^2$ | X | m/p |
|---|---|---|
| n-Hex | O | m/p = 7.4 |
| ⸺⟨⟩⸺OMe | O | m/p = 14 |
| ⸺⟨⟩⸺CF$_3$ | O | m/p = 7.2 |
| ⸺⟨⟩⸺n-Bu | O | m/p = 3.9 |
| ⸺⟨2,6-dimethylphenyl⟩ | O | m/p = 3.6 |

Example 10

(1) The borylation reaction was performed by using alkoxycarbonyl-substituted pyridines and alkoxycarbonylmethyl-substituted pyridines as the substituted aromatic compounds, the substrates of the borylation reaction, in the same manner as Example 9(1).

In a dried test tube, to a p-xylene (1.5 mL) solution of an alkoxycarbonyl-substituted pyridine (1.00 equiv), [Ir(OMe)(cod)]$_2$ (1.5 mol %), 1-(2-([2,2'-bipyridin]-5-yl)phenyl)-3-(4-trifluoromethylphenyl)urea (3.0 mol %) and bis(pinacolato)diboron (1.5 equiv) were added and stirred at 25° C. for 18 hours. The solvent was removed under reduced pressure, and then the products were isolated and prepared by recycling preparative HPLC.

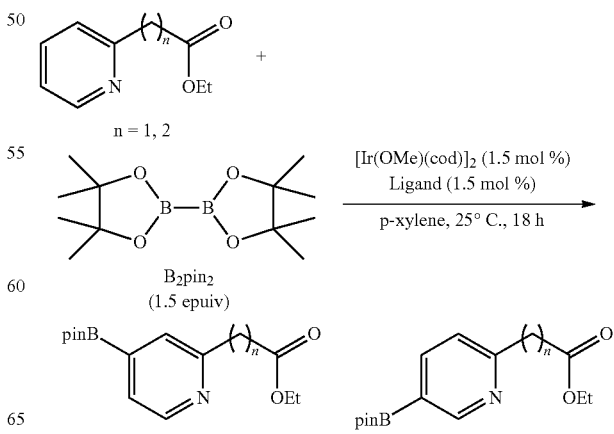

The obtained compounds were as follows.

Ethyl-5-(4,4,5,5-tetramethyl-1,3,2-dioxaborolan-2-yl)pyridine-2-carboxylate and ethyl-4-(4,4,5,5-tetramethyl-1,3,2-dioxaborolan-2-yl)pyridine-2-carboxylate

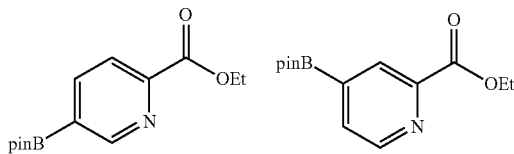

70% yield [5-/4-=5.0]; white solid; $^{13}$C NMR (100 MHz, CDCl$_3$) δ (4- and 5-position isomers) 25.0 (4- and 5-position isomers), 35.71, 35.76, 39.0, 39.1, 84.6, 84.8, 122.7, 128.5, 129.3, 143.4, 147.9, 154.07, 154.13, 156.5, 169.4 (4- and 5-position isomers); $^{11}$B NMR (130 MHz, CDCl3) δ 30.6; IR (neat, v/cm$^{-1}$) 2979, 1640, 1473, 1358, 1263, 1105, 965, 857, 752, 672; HRMS (ESI$^+$) Calcd for C$_{14}$H$_{21}$BN$_2$NaO$_3$ ([M+Na]$^+$) 299.1537, Found 299.1534.

Ethyl-5-(4,4,5,5-tetramethyl-1,3,2-dioxaborolan-2-yl)pyridine-2-carboxylate: $^1$H NMR (500 MHz, CDCl$_3$) δ 1.36 (s, 12H), 3.04 (s, 3H), 3.13 (s, 3H), 7.58 (d, J=7.8 Hz, 1H), 8.15 (d, J=7.8 Hz, 1H), 8.91 (s, 1H). Ethyl-4-(4,4,5,5-tetramethyl-1,3,2-dioxaborolan-2-yl)pyridine-2-carboxylate: $^1$H NMR (500 MHz, CDCl$_3$) δ 1.34 (s, 12H), 3.04 (s, 3H), 3.13 (s, 3H), 7.65 (d, J=5.8 Hz, 1H), 7.96 (s, 1H), 8.60 (d, J=5.8 Hz, 1H).

By using the ligand used in (1), the following compounds were obtained in the same manner as the method of (1).

(2) 2-Ethoxycarbonylmethyl-5-(4,4,5,5-tetramethyl-1,3,2-dioxaborolan-2-yl)pyridine and 2-ethoxycarbonylmethyl-4-(4,4,5,5-tetramethyl-1,3,2-dioxaborolan-2-yl)pyridine

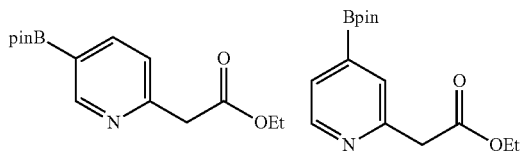

64% yield [5-/-4-=1.7]; pale brown oil; $^{11}$B NMR (130 MHz, CDCl$_3$) δ 30.9; IR (neat, v/cm$^{-1}$) 2980, 2934, 1739, 1600, 1557, 1480, 1403, 1371, 1258, 1166, 1145, 1099, 1028, 964, 856, 668; HRMS (ESI$^+$) Calcd for C$_{15}$H$_{22}$BNNaO$_4$ ([M+Na]$^+$) 314.1540, Found 314.1539.

2-Ethoxycarbonylmethyl-5-(4,4,5,5-tetramethyl-1,3,2-dioxaborolan-2-yl)pyridine: $^1$H NMR (500 MHz, CDCl$_3$) δ 1.18-1.25 (m, 3H), 1.32 (s, 12 H), 3.83 (s, 2H), 4.10-4.20 (m, 2H), 7.26 (d, J=8.0 Hz, 1H), 8.00 (d, J=8.0 Hz, 1H), 8.86 (s, 1H); $^{13}$C NMR (100 MHz, CDCl$_3$) δ 14.1, 24.7, 44.1, 61.0, 84.1, 123.1, 142.9, 155.2, 156.8, 170.4.

2-Ethoxycarbonylmethyl-4-(4,4,5,5-tetramethyl-1,3,2-dioxaborolan-2-yl)pyridine: $^1$H NMR (500 MHz, CDCl$_3$) δ 1.18-1.25 (m, 3H), 1.32 (s, 12H), 3.82 (s, 2H), 4.10-4.20 (m, 2H), 7.50 (d, J=4.6 Hz, 1H), 7.60 (s, 1H), 8.56 (d, J=4.6 Hz, 1H); $^{13}$C NMR (100 MHz, CDCl$_3$) δ 14.1, 24.8, 43.8, 60.9, 84.4, 127.0, 128.9, 148.9, 153.8, 170.7.

Example 11

(1) The borylation reaction was performed by using a phosphate-, phosphinediamide- or phosphine oxide-substituted benzene as the substituted aromatic compound, the substrate of the borylation reaction, in the same manner as Example 9.

In a dried test tube, to a p-xylene (1.5 mL) solution of a phosphate-, phosphinediamide- or phosphine oxide-substituted benzene (1.00 equiv), [Ir(OMe)(cod)]$_2$ (1.5 mol %), 1-(2-([2,2'-bipyridin]-5-yl)phenyl)-3-cyclohexylurea (3.0 mol %) and bis(pinacolato)diboron (1.5 equiv) were added and stirred at 25° C. or 40° C. for 16 hours. The solvent was removed under reduced pressure, and then the products were isolated and prepared by recycling preparative HPLC.

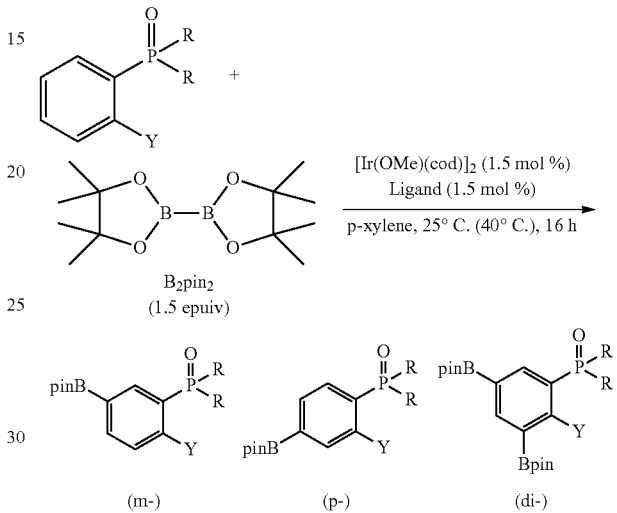

(wherein R represents an ethoxy group, a diethylamino group or a cyclohexyl group(abbreviated as Cy), and Y represents H, Br, Cl, CF$_3$, OMe or Me).

The obtained compounds were as follows.

3-(4,4,5,5-Tetramethyl-1,3,2-dioxaborolan-2-yl)phenyldiethylphosphonate and 4-(4,4,5,5-tetramethyl-1,3,2-dioxaborolan-2-yl)phenyldiethylphosphonate

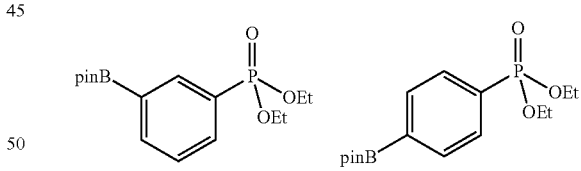

41% yield [meta/para=17]; colorless solid; $^{11}$B NMR (130 MHz, CDCl3) δ 30.7; $^{31}$P NMR (158 MHz, CDCl$_3$) δ 28.5, 28.1; IR (KBr, v/cm$^{-1}$) 2980, 1599, 1481, 1408, 1390, 1358, 1324, 1243, 1211, 1133, 1136,1097, 1055, 1027, 965, 869, 843, 795, 767, 704, 669; HRMS (ESI$^+$) Calcd for C$_{16}$H$_{26}$BO$_5$P ([M+Na]$^+$) 363.1509, Found 363.1498.

3-(4,4,5,5-Tetramethyl-1,3,2-dioxaborolan-2-yl)phenyldiethylphosphonate: $^1$H NMR (400 MHz, CDCl$_3$) δ 1.30 (t, J=7.2 Hz, 6H), 1.32 (s, 12H), 3.98-4.18 (m, 4H), 7.44 (ddd, J=7.6, 7.6, 4.0 Hz, 1H), 7.88 (ddd, J=13.0, 7.6, 1.3 Hz, 1H), 7.95 (dd, J=7.6, 1.3 Hz, 1H),8.24 (d, J=13.0 Hz, 1H), $^{13}$C NMR (100 MHz, CDCl$_3$) δ 16.3 (d, J$_{C-P}$=6.6 Hz), 24.8, 62.0 (d, J$_{C-P}$=5.8 Hz), 84.0, 127.6 (d, J$_{C-P}$=187 Hz), 127.7 (d, J$_{C-P}$=15.0 Hz), 134.3 (d, J$_{C-P}$=10.3 Hz), 138.0 (d, J$_{C-P}$=9.4 Hz),138.6 (d, J$_{C-P}$2.8 Hz).

4-(4,4,5,5-Tetramethyl-1,3,2-dioxaborolan-2-yl)phenyldiethylphosphonate: $^1$H NMR (400 MHz, CDCl$_3$) δ 1.30 (t, J=7.2 Hz, 6H),1.32 (s, 12H), 3.98-4.18 (m, 4H), 7.78 (dd, J=13.0, 8.0 Hz, 2H),7.88 (dd, J=8.0, 4.0 Hz, 2H); $^{13}$C NMR (100 MHz, CDCl$_3$) δ 16.3 (d, $J_{C-P}$=6.6 Hz), 24.8, 62.0 (d, $J_{C-P}$=5.8 Hz), 84.0, 130.9 (d, $J_{C-P}$=185 Hz), 130.8 (d, $J_{C-P}$=9.4 Hz), 134.5 (d, $J_{C-P}$=15.0 Hz).

3,5-Bis(4,4,5,5-tetramethyl-1,3,2-dioxaborolan-2-yl)phenyldiethylphosphonate

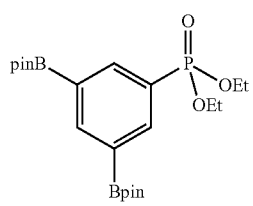

16% yield; colorless solid; $^1$H NMR (400 MHz, CDCl$_3$) δ 1.31 (t, J=7.2 Hz, 6H), 1.33 (s, 24H), 3.99-4.20 (m, 4H), 8.32 (dd, J=13.0, 1.4 Hz, 1H), 8.40 (d, J=1.4 Hz, 1H); $^{13}$C NMR (100 MHz, CDCl$_3$) δ 16.3 (d, $J_{C-P}$=6.6 Hz), 24.8, 62.0 (d, $J_{C-P}$=5.6 Hz), 84.0, 127.0 (d, $J_{C-P}$=187 Hz), 140.7 (d, $J_{C-P}$=10.3 Hz), 144.9 (d, $J_{C-P}$=1.9 Hz); $^{11}$B NMR (130 MHz, CDCl3) δ 31.0; $^{31}$P NMR (158 MHz, CDCl$_3$) δ 30.4; IR (KBr, v/cm$^{-1}$) 2977, 1597, 1389, 1331, 1318, 1272, 1248, 1214, 1168, 1141, 1048, 1019, 964, 952, 886, 848, 790, 718, 691,662; HRMS (ESI$^+$) Calcd for C$_{22}$H$_{37}$B$_2$NaO$_7$P ([M+Na]$^+$) 489.2361, Found 489.2364.

By using the ligand used in (1), the following compounds ((2) to (9)) were obtained in the same manner as the method of (1).

(2) (2-Methoxy-5-(4,4,5,5-tetramethyl-1,3,2-dioxaborolan-2-yl)phenyldiethylphosphonate and (2-methoxy-4-(4,4,5,5-tetramethyl-1,3,2-dioxaborolan-2-yl)phenyldiethylphosphonate

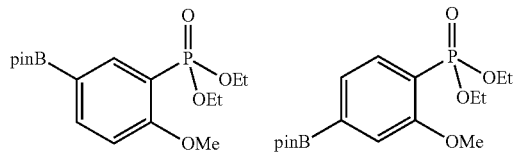

59% yield [meta/para=0.54]; pale brown oil; $^{11}$B NMR (130 MHz, CDCl$_3$) δ 30.7; $^{31}$P NMR (158 MHz, CDCl$_3$) δ 28.1, 28.5; IR (neat, v/cm$^{-1}$) 2979, 2935, 2909, 1597, 1550, 1492, 1462, 1393, 1357,1325, 1244, 1164, 1146, 1108, 1078, 1055, 1029, 965, 903, 851, 777, 760, 692, 675; HRMS (ESI$^+$) Calcd for C$_{17}$H$_{28}$BNaO$_6$P ([M+Na]$^+$) 393.1614, Found 393.1599.

(2-Methoxy-5-(4,4,5,5-tetramethyl-1,3,2-dioxaborolan-2-yl)phenyldiethylphosphonate: $^1$H NMR (500 MHz, CDCl$_3$) δ 1.15-1.45 (m, 18H), 3.88 (s, 3H), 4.00-4.25 (m, 4H), 6.85-6.92 (m, 1H), 7.91 (d, J=8.6 Hz, 1H),8.24 (d, J=14.9 Hz, 1H), $^{13}$C NMR (125 MHz, CDCl$_3$) δ 16.3, 24.8, 55.6, 62.0 (d, $J_{C-P}$=4.8 Hz), 83.7, 110.3 (d, $J_{C-P}$=8.4 Hz), 115.8 (d, $J_{C-P}$=186 Hz), 141.1, 142.0 (d, $J_{C-P}$=7.2 Hz), 163.5 (d, $J_{C-P}$=2.4 Hz).

(2-Methoxy-4-(4,4,5,5-tetramethyl-1,3,2-dioxaborolan-2-yl)phenyldiethylphosphonate: $^1$H NMR (500 MHz, CDCl$_3$) δ 1.15-1.45 (m, 18H), 3.91 (s, 3H), 4.00-4.25 (m, 4H), 7.31 (d, J=6.3 Hz, 1H), 7.41 (dd, J=7.5, 3.4 Hz, 1H), 7.78 (dd, J=14.3, 7.5 Hz, 1H); $^{13}$C NMR (125 MHz, CDCl$_3$) δ 16.2, 24.8, 55.8, 62.1 (d, $J_{C-P}$=6.0 Hz), 84.1, 116.5 (d, $J_{C-P}$=8.4 Hz), 119.0 (d, $J_{C-P}$=185 Hz), 126.5 (d, $J_{C-P}$=14.4 Hz), 134.2 (d, $J_{C-P}$=7.2 Hz), 160.5(d, $J_{C-P}$=2.4 Hz).

(3) (2-Methyl-5-(4,4,5,5-tetramethyl-1,3,2-dioxaborolan-2-yl)phenyldiethylphosphonate and (2-methyl-4-(4,4,5,5-tetramethyl-1,3,2-dioxaborolan-2-yl)phenyldiethylphosphonate

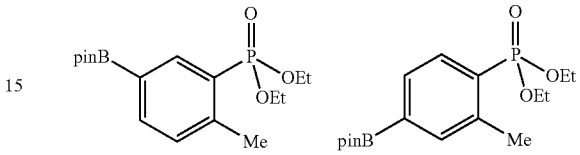

66% yield [meta/para=9.0]; pale yellow oil; $^{11}$B NMR (130 MHz, CDCl$_3$) δ 30.9; $^{31}$P NMR (158 MHz, CDCl$_3$) δ 30.7, 30.2; IR (neat, v/cm$^{-1}$) 2979, 2931, 2906, 1603, 1480, 1445, 1386, 1360, 1317,1248, 1165, 1147, 1109, 1049, 1023, 963, 851, 795, 728, 674; HRMS (ESI$^+$) Calcd for C$_{17}$H$_{28}$BNaO$_5$P ([M+Na]$^+$) 377.1665, Found 337.1666.

(2-Methyl-5-(4,4,5,5-tetramethyl-1,3,2-dioxaborolan-2-yl)phenyldiethylphosphonate: $^1$H NMR (500 MHz, CDCl$_3$) δ 1.23-1.38 (m, 18H), 2.56 (s, 3H),4.01-4.18 (m, 4H), 7.24 (dd, J=7.5, 5.2 Hz, 1H), 7.81 (d, J=7.5 Hz, 1H), 8.33 (d, J=14.4 Hz, 1H); $^{13}$C NMR (100 MHz, CDCl$_3$) δ 16.2 (d, $J_{C-P}$=6.1 Hz), 21.4 (d, $J_{C-P}$=3.3 Hz), 24.8, 61.7 (d, p=5.6 Hz), 83.8, 126.2 (d, $J_{C-P}$=183 Hz), 130.5 (d, $J_{C-P}$=14.1 Hz), 138.6 (d, $J_{C-P}$=2.8 Hz), 140.4 (d, $J_{C-P}$=10.3 Hz), 144.8 (d, $J_{C-P}$=10.3 Hz).

(2-Methyl-4-(4,4,5,5-tetramethyl-1,3,2-dioxaborolan-2-yl)phenyldiethylphosphonate: $^1$H NMR (500 MHz, CDCl$_3$) δ 1.23-1.38 (m, 18H), 2.56 (s, 3H), 4.00-4.17 (m, 4H), 7.65-7.70 (m, 2H), 7.88 (dd, J=14.3, 8.0 Hz, 1H); $^{13}$C NMR (100 MHz, CDCl$_3$) δ 16.2 (d, $J_{C-P}$=6.6 Hz), 20.9 (d, $J_{C-P}$=2.8 Hz), 24.8, 61.7 (d, $J_{C-P}$=5.6 Hz), 84.0, 129.4 (d, $J_{C-P}$=181 Hz), 131.5 (d, $J_{C-P}$=14.4 Hz), 133.0 (d, $J_{C-P}$=10.8 Hz), 137.2 (d, $J_{C-P}$=14.4 Hz), 140.7 (d, $J_{C-P}$=10.8 Hz).

(4) (2-Bromo-5-(4,4,5,5-tetramethyl-1,3,2-dioxaborolan-2-yl)phenyl)diethylphosphonate

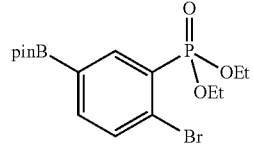

65% yield; pale yellow oil; $^1$H NMR (400 MHz, CDCl$_3$) δ 1.29 (s, 12H), 1.32 (t, J=7.2 Hz, 6H), 4.02-4.22 (m, 4H), 7.63 (dd, J=8.1, 4.9 Hz, 1H), 7.73 (dd, J=8.1, 1.3 Hz, 1H), 8.41 (d, J=13.9, 1.3 Hz, 1H); $^{13}$C NMR (125 MHz, CDCl$_3$) δ 16.2 (d, $J_{C-P}$=7.2 Hz), 24.8, 62.4 (d, $J_{C-P}$=4.8 Hz), 84.2, 128.6 (d, $J_{C-P}$=4.8 Hz), 128.7 (d, $J_{C-P}$=191 Hz), 133.6 (d, $J_{C-P}$=9.6 Hz),139.5 (d, $J_{C-P}$=2.4 Hz), 142.6 (d, $J_{C-P}$=8.4 Hz); $^{11}$B NMR (130 MHz, CDCl$_3$) δ 30.9; $^{31}$P NMR (158 MHz, CDCl$_3$) δ 26.1; IR (neat, v/cm$^{-1}$) 2979, 2932, 2906, 1585, 1552,1476, 1444, 1373, 1356, 1319, 1262, 1251, 1214, 1166, 1145, 1098, 1054, 1024, 964,845, 796, 766, 726, 671; HRMS (ESI$^+$) Calcd for C$_{16}$H$_{25}$BBrNaO$_5$P ([M+Na]$^+$) 441.0614, Found 441.0602.

(5) (5-(4,4,5,5-Tetramethyl-1,3,2-dioxaborolan-2-yl)-2-trifluoromethylphenyl)diethylphosphonate

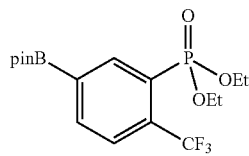

30% yield; pale yellow solid; $^1$H NMR (500 MHz, CDCl$_3$) δ 1.28-1.40 (m, 18H), 4.07-4.26 (m, 4H), 7.78 (dd, J=8.0, 5.7 Hz, 1H), 8.05 (d, J=8.0 Hz, 1H), 8.64 (d, J=14.9 Hz, 1H); $^{13}$C NMR (100 MHz, CDCl$_3$) δ 16.1 (d, $J_{C-P}$=6.6 Hz), 24.8, 62.6 (d, $J_{C-P}$=6.1 Hz), 84.5, 121.9 (qd, $J_{C-P, C-P}$=273, 4.7 Hz), 126.0 (d, $J_{C-P}$=184 Hz), 127.4 (dq, $J_{C-P, C-P}$=6.1, 10.8 Hz), 134.3 (qd, $J_{C-P, C-P}$=32.4, 7.5 Hz), 138.6 (d, $J_{C-P}$=2.8 Hz), 142.1 (d, $J_{C-P}$=15.4 Hz); $^{11}$B NMR (130 MHz, CDCl$_3$) δ 30.8; $^{19}$F NMR (368 MHz, CDCl$_3$) δ −60.9 (s, 3F); $^{31}$P NMR (158 MHz, CDCl$_3$) δ 26.1; IR (KBr, ν/cm$^{-1}$) 2993, 1377, 1362,1325, 1308, 1280, 1244, 1148, 1135, 1104, 1059, 1029, 977, 964, 951, 849, 768, 682; HRMS (ESI$^+$) Calcd for C$_{17}$H$_{25}$BF$_3$NaO$_5$P ([M+Na]$^+$) 431.1382, Found 431.1379.

(6) N,N,N',N'-Tetraethyl-P-(3-(4,4,5,5-tetramethyl-1,3,2-dioxaborolan-2-yl)phenyl)phosphonic diamide

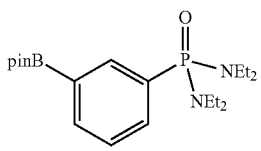

296 yield; pale brown oil; $^1$H NMR (500 MHz, CDCl$_3$) δ 1.04 (t, J=7.5 Hz, 12H), 1.33 (s, 12H), 3.00-3.13 (m, 8H), 7.35-7.47 (m, 1H), 7.84 (dd, J=11.5, 7.5 Hz, 1H), 7.88 (d, J=6.9 Hz, 1H), 8.19 (d, J=11.5 Hz, 1H); $^{13}$C NMR (125 MHz, CDCl$_3$) δ 13.6 (d, $J_{C-P}$=2.4 Hz), 24.9, 38.4 (d, JC-P=4.8 Hz), 83.9, 127.5 (d, $J_{C-P}$=12.0 Hz), 132.4 (d, $J_{C-P}$=158 Hz), 134.5 (d, $J_{C-P}$=8.4 Hz), 137.2, 138.3 (d, $J_{C-P}$=8.4 Hz); $^{11}$B NMR (130 MHz, CDCl$_3$) δ 31.5; $^{31}$P NMR (158 MHz, CDCl$_3$) δ 39.4; IR (neat, ν/cm$^{-1}$) 2973, 2932, 2871, 1594, 1470, 1383, 1357, 1317, 1262, 1216, 1187, 1015, 945, 866, 841, 791, 739, 711, 671, 656; HRMS (ESI$^+$) Calcd for C$_{20}$H$_{37}$BN$_2$O$_3$P ([M+H]$^+$) 395.2635, Found 395.2639.

N,N,N',N'-Tetraethyl-P-(3,5-bis(4,4,5,5-tetramethyl-1,3,2-dioxaborolan-2-yl)phenyl)phosphonic diamide

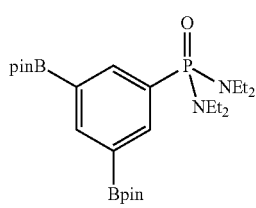

9% yield; pale brown solid; $^1$H NMR (500 MHz, CDCl$_3$) δ 1.03 (t, J=6.9 Hz, 12H), 1.31 (s, 24H), 2.98-3.16 (m, 8H), 8.27 (d, J=12.1 Hz, 2H), 8.32 (s, 1H); $^{13}$C NMR (125 MHz, CDCl) δ 13.6 (d, $J_{C-P}$=2.4 Hz), 24.8, 38.3 (d, $J_{C-P}$=3.6 Hz), 83.8, 131.8 (d, $J_{C-P}$=154 Hz), 141.1 (d, $J_{C-P}$=9.6 Hz), 143.5 (d, $J_{C-P}$=2.4 Hz); $^{11}$B NMR (130 MHz, CDCl3$_3$) δ 31.3; $^{31}$P NMR (158 MHz, CDCl$_3$) δ 39.5; IR (KBr, ν/cm$^{-1}$) 2978, 2932, 2873, 1594, 1458, 1383, 1327,1313, 1272, 1220, 1189, 1163, 1144, 1020, 967, 945, 887, 847, 720, 659; HRMS (ESI$^+$)Calcd for C$_{26}$H$_{47}$B$_2$N$_2$NaO$_5$P ([M+Na]$^+$) 543.3306, Found 543.3312.

(7) Dicyclohexyl(3-(4,4,5,5-tetramethyl-1,3,2-dioxaborolan-2-yl)phenyl)phosphine oxide

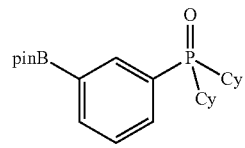

39% yield; pale brown solid; $^1$H NMR (500 MHz, CDCl$_3$) δ 1.05-1.37 (m, 21H), 1.50-1.88 (m, 8H), 1.90-2.20 (m, 4H), 2.25-2.46 (m, 1H), 7.40-7.51 (m, 1H),7.68-7.83 (m, 1H), 7.93 (d, J=6.9 Hz, 1H), 7.98-8.07 (m, 1H); $^{13}$C NMR (125 MHz, CDCl$_3$) δ 24.6, 24.9, 25.5, 25.8, 26.2-26.5 (m, 2C), 35.2 (d, $J_{C-P}$=66.0 Hz), 84.0, 127.4-127.6 (m), 129.1 (d, $J_{C-P}$=85.2 Hz), 134.1-134.4 (m), 137.2-137.5 (m), 137.6; $^{11}$B NMR (130 MHz, CDCl$_3$) δ 30.9; $^{31}$P NMR (158 MHz, CDCl$_3$) δ 56.7; IR (KBr, ν/cm$^{-1}$) 2979, 2930, 2853, 1594, 1449, 1404, 1359, 1316, 1273, 1211, 1166, 1145, 1130, 1115, 1077, 963, 891, 853, 840, 759, 731, 709, 671; HRMS (ESI$^+$) Calcd for C$_{24}$H$_{38}$BNaO$_3$P ([M+Na]$^+$) 439.2549, Found 439.2567.

Dicyclohexyl(3,5-bis(4,4,5,5-tetramethyl-1,3,2-dioxaborolan-2-yl)phenyl)phosphine oxide

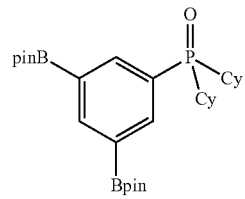

35% yield; pale brown solid; $^1$H NMR (500 MHz, CDCl$_3$) δ 1.08-1.36 (m, 33H), 1.51-1.86 (m, 8H), 1.94-2.13 (m, 4H), 2.23-2.45 (m, 1H), 8.11 (d, J=9.8 Hz, 1H), 8.37 (s, 1H); $^{13}$C NMR (125 MHz, CDCl$_3$) δ 24.7, 24.8, 25.5, 25.8, 26.2-26.5 (m, 2C), 35.3 (d, $J_{C-P}$=67.2 Hz), 84.0, 128.5 (d, $J_{C-P}$=85.2 Hz), 140.2 (d, $J_{C-P}$=7.2 Hz), 144.0; $^{11}$B NMR (130 MHz, CDCl$_3$) δ 31.2; $^{31}$P NMR (158 MHz, CDCl$_3$) δ 56.4; IR (KBr, ν/cm$^{-1}$) 2977, 2929, 2853, 1594, 1449, 1383, 1329, 1272, 1215, 1176, 1143, 966, 888, 849, 716; HRMS (ESI$^+$) Calcd for C$_{30}$H$_{50}$B$_2$O$_5$P ([M+H]$^+$) 543.3582, Found. 543.3588.

(8) Dicyclohexyl(2-methoxy-5-(4,4,5,5-tetramethyl-1,3,2-dioxaborolan-2-yl)phenyl)phosphine oxide

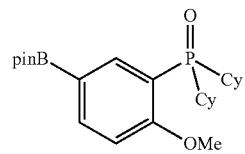

99% yield; pale yellow solid; $^1$H NMR (400 MHz, CDCl$_3$) δ 1.14-1.19 (m, 4H), 1.21-1.42 (m, 16H), 1.44-1.51 (m, 4H), 1.64-1.68 (m, 4H), 1.80-1.84 (m, 2H), 2.03-2.17 (m, 4H), 3.86 (s, 3H), 6.87 (dd, J=8.7, 4.7 Hz, 1H), 7.91 (d, J=8.7 Hz, 1H), 8.36 (d, J=11.7 Hz, 1H); $^{13}$C NMR (100 MHz, CDCl$_3$) δ 24.9, 25.7 (d, J$_{C-P}$=3.8 Hz), 25.9, 26.1 (d, J$_{C-P}$=3.8 Hz), 26.6 (d, J$_{C-P}$=12.3 Hz), 26.9 (d, J$_{C-P}$=14.1 Hz), 36.9 (d, J$_{C-P}$=67.7 Hz), 55.1, 83.7, 109.3 (d, J$_{C-P}$=6.9 Hz), 118.3 (d, J$_{C-P}$=83.8 Hz), 140.1 (d, J$_{C-P}$=1.9 Hz), 142.8 (d, J$_{C-P}$=3.8 Hz), 161.5 (d, J$_{C-P}$=5.6 Hz); $^{11}$B NMR (130 MHz, CDCl$_3$) δ 29.8; $^{31}$P NMR (158 MHz, CDCl$_3$) δ 59.5; IR (KBr, v/cm$^{-1}$) 2978, 2931, 2852, 1594, 1448, 1407, 1385, 1357, 1317, 1279, 1266, 1250, 1212, 1147, 1104, 1077, 1014, 964, 887, 851, 824, 750, 673; HRMS (ESI$^+$) Calcd for C$_{25}$H$_{40}$BNaO$_4$P ([M+Na]$^+$) 469.2655, Found 469.2668.

(9) Dicyclohexyl(2-chloro-5-(4,4,5,5-tetramethyl-1,3,2-dioxaborolan-2-yl)phenyl)phosphine oxide

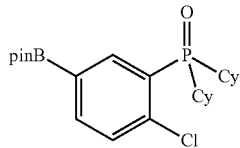

99% yield; pale yellow solid; $^1$H NMR (400 MHz, CDCl$_3$) δ 1.16-1.21 (m, 4H), 1.24-1.36 (m, 18H), 1.59-1.70 (m, 6H), 1.83-1.86 (m, 2H), 2.07-2.10 (m, 2H), 2.27-2.36 (m, 2H), 7.36 (dd, J=7.9, 3.6 Hz, 1H), 7.81 (d, J=7.9 Hz, 1H), 8.49 (d, J=10.5 Hz, 1H); $^{13}$C NMR (100 MHz, CDCl$_3$) δ 24.9, 25.7 (d, J$_{C-P}$=1.4 Hz), 26.2 (d, J$_{C-P}$=3.3 Hz), 26.3 (d, J$_{C-P}$=3.8 Hz), 26.5 (d, J$_{C-P}$=12.7 Hz), 26.7 (d, J$_{C-P}$=13.6 Hz), 37.4 (d, J$_{C-P}$=13.6 HZ), 84.2, 129.3 (d, J$_{C-P}$=6.1 Hz), 130.1, 137.3 (d, J$_{C-P}$=6.1 HZ), 138.8 (d, J$_{C-P}$=2.3 Hz), 143.1 (d, J$_{C-P}$=4.7 Hz); $^{11}$B NMR (130 MHz, CDCl$_3$) δ 30.5; $^{31}$P NMR (158 MHz, CDCl$_3$) δ 59.4; IR (KBr, v/cm$^{-1}$) 2978, 2932, 2852, 1583, 1557, 1448, 1371, 1356, 1317, 1259, 1214, 1183, 1169, 1143, 1113, 1097, 1031, 964, 845, 755, 726, 671; HRMS (ESI$^+$) Calcd for C$_{24}$H$_{38}$BClO$_3$P ([14+H]$^+$) 451.2340, Found 451.2341.

The invention claimed is:

1. A bipyridyl compound represented by a formula (1):

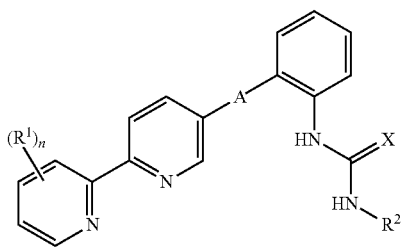

wherein A represents a single bond at an ortho-position relative to the uredio group;

X represents an oxygen atom;

n pieces of R$^1$ may be the same or different, and R$^1$ represents a hydrogen atom, a halogen atom, a C$_{1-10}$ alkyl group, a C$_{2-10}$ alkenyl group, a C$_{3-7}$ cycloalkyl group, a C$_{6-10}$ aryl group, an optionally substituted alkoxy group, an optionally substituted aryloxy group, an optionally substituted amino group, a cyano group, a nitro group, or an alkoxycarbonyl group, or two adjacent R$^1$ may form a saturated or unsaturated ring structure optionally containing a hetero atom together with the carbon atoms bonded to the two R$^1$;

R$^2$ represents a hydrogen atom, an unsubstituted C$_{1-16}$ hydrocarbon group, a C$_{1-16}$ hydrocarbon group substituted with a halogen, a C$_{1-6}$ alkoxy group, a C$_{1-6}$ alkyl group, or a halgeno-C$_{1-6}$ alkyl group, an optionally substituted alkoxy group, or an optionally substituted aryloxy group; and n represents a number of 1 to 4, wherein the optional substitution on the hydrocarbon group of R$^1$ is 1 to 3 halogen atoms, a cyano group, a nitro group, a halogeno C$_{1-6}$ alkyl group or a C$_{1-6}$ alkoxy group, wherein the optional substitution on the alkoxy group and the aryloxy group of R$^1$ is 1 to 3 halogen atoms, a cyano group, a nitro aroup, a halogeno C$_{1-6}$ alkyl group or a C$_{1-6}$ alkoxy group, wherein the optional substitution on the amino group of R$^1$ is a C$_{1-6}$ alkyl group or a halogeno C$_{1-6}$ alkyl group, wherein the optional substitution on the hydrocarbon group of R$^2$ is 1 to 3 halogen atoms, a cyano group, a nitro group, a halogeno C$_{1-6}$ alkyl group or a C$_{1-6}$ alkoxy group, wherein the optional substitution on the alkoxy group and the aryloxy group of R$^2$ is 1 to 3 halogen atoms, a cyano group, a nitro group, a halogeno C$_{1-6}$ alkyl group or a C$_{1-6}$ alkoxy group.

2. The bipyridyl compound according to claim 1, wherein R$^1$ is a hydrogen atom, a halogen atom, an alkyl group having 1 to 10 carbon atoms, an alkenyl group having 2 to 10 carbon atoms, a cycloalkyl group having 3 to 7 carbon atoms, an aryl group having 6 to 10 carbon atoms, an aryloxy group having 6 to 10 carbon atoms, an alkoxy group having 1 to 10 carbon atoms, a C$_{1-6}$ alkylamino group, a di(C$_{1-6}$ alkyl)amino group or a C$_{1-10}$ alkoxycarbonyl group.

3. The bipyridyl compound according to claim 1, wherein R$^2$ is a hydrogen atom, an optionally substituted alkyl group having 1 to 10 carbon atoms, an optionally substituted alkenyl group having 2 to 10 carbon atoms, an optionally substituted cycloalkyl group having 3 to 7 carbon atoms, an optionally substituted aryl group having 6 to 10 carbon atoms, an optionally substituted alkoxy group having 1 to 10 carbon atoms or an optionally substituted aryloxy group having 6 to 10 carbon atoms.

4. The bipyridyl compound according to claim 1, wherein when R$^2$ is a substituted non-heterocyclic group, the substitution is selected from the group consisting of 1 to 3 halogen atoms, a cyano group, a halogeno C$_{1-6}$ alkyl group and a C$_{1-6}$ alkoxy group.

5. The bipyridyl compound according to claim 1, which is 1-(2-([2,2'-Bipyridin]-5-yl)phenyl-3-(4-methoxyphenyl)urea.

6. The bipyridyl compound according to claim 1, which is 1-(2-([2,2'-Bipyridin]-5-yl)pheryl)-3-cyclohexylthiourea.

7. The bipyridyl compound according to claim 1, which is 1-(2-([2,2'-Bipyridin]-5-ylethynyl)phenyl)-3-phenylurea.

8. The bipyridyl compound according to claim 1, wherein R$^1$ is a hydrogen atom.

9. The bipyridyl compound according to claim 1, wherein A represents a single bond or an ethynylene group.

10. The bipyridyl compound according to claim 1, wherein R$^1$ represents a hydrogen atom, a halogen atom, an optionally substituted hydrocarbon group, an optionally substituted alkoxy group, an optionally substituted aryloxy group, an optionally substituted amino group, a cyano group, a nitro group, or an alkoxycarbonyl group.

11. The bipyridyl compound according to claim 9, wherein $R^1$ represents a hydrogen atom, a halogen atom, an optionally substituted hydrocarbon group, an optionally substituted alkoxy group, an optionally substituted aryloxy group, an optionally substituted amino group, a cyano group, a nitro group, or an alkoxycarbonyl group.

12. The bipyridyl compound according to claim 1, wherein when $R_2$ is an unsubstituted $C_{1-16}$ hydrocarbon group or a C1-16 hydrocarbon group substituted with a $C_{1-10}$ alkyl group, a $C_{3-7}$ cycoalkyl group or a phenyl group.

* * * * *